United States Patent
Pinto et al.

(10) Patent No.: US 6,750,225 B2
(45) Date of Patent: *Jun. 15, 2004

(54) 1,4,5,6-TETRAHYDROPYRAZOLO-[3,4,-C]-PYRIDIN-7-ONES USEFUL AS FACTOR XA INHIBITORS

(75) Inventors: Donald Joseph Philip Pinto, Kennett Square, PA (US); Robert Anthony Galemmo, Jr., Collegeville, PA (US); Michael James Orwat, Hockessin, DE (US); Mimi Lifen Quan, Newark, DE (US)

(73) Assignee: Bristol-Myers Squibb Pharms Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/124,383

(22) Filed: Apr. 17, 2002

(65) Prior Publication Data
US 2002/0177713 A1 Nov. 28, 2002

Related U.S. Application Data
(60) Provisional application No. 60/284,615, filed on Apr. 18, 2001.

(51) Int. Cl.$^7$ .................... A61K 31/437; C07D 471/04; A61P 7/02
(52) U.S. Cl. ......................................... 514/303; 546/119
(58) Field of Search ........................... 546/119; 514/303

(56) References Cited

U.S. PATENT DOCUMENTS

| 3,340,269 A | 9/1967 | Blatter | |
| 3,365,459 A | 1/1968 | Blatter | |
| 3,423,414 A | 1/1969 | Blatter | |
| 6,413,980 B1 * | 7/2002 | Fevig et al. | 514/300 |
| 2003/0018023 A1 * | 1/2003 | Pinto et al. | 514/215 |

FOREIGN PATENT DOCUMENTS

| WO | WO 9501980 | 1/1995 |
| WO | WO 9612720 | 5/1996 |
| WO | WO 9852948 | 11/1998 |
| WO | WO 0039131 | 7/2000 |
| WO | WO 0119798 | 3/2001 |

* cited by examiner

*Primary Examiner*—Evelyn Mei Huang
(74) *Attorney, Agent, or Firm*—David H. Vance; Jing S. Belfield

(57) ABSTRACT

The present application describes 1,4,5,6-tetrahydropyrazolo-[3,4-c]-pyridin-7-ones of the following formula or pharmaceutically acceptable salt forms thereof:

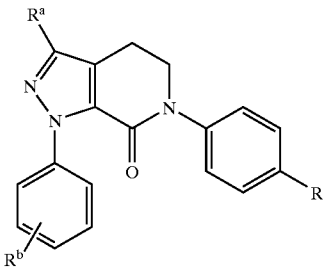

wherein ring $R^b$ is 3-amido or 4-methoxy, $R^a$ can be cyano, trifluoromethyl, or amido, and R can be a substituted phenyl, a substituted imidazolyl, or a substituted pyridine. Compounds of the present invention are useful as inhibitors of trypsin-like serine proteases, specifically factor Xa.

65 Claims, No Drawings

1,4,5,6-TETRAHYDROPYRAZOLO-[3,4,-C]-PYRIDIN-7-ONES USEFUL AS FACTOR XA INHIBITORS

CROSS-REFERENCE TO RELATED APPLICATIONS

This application claims the priority benefit of U.S. Provisional Application No. 60/284,615 filed Apr. 18, 2001, which is incoporated herein by reference.

FIELD OF THE INVENTION

This invention relates generally to 1,4,5,6-tetrahydropyrazolo-[3,4-c]-pyridin-7-ones, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO95/01980 and WO96/12720 describe phosphodiesterase type IV and TNF production inhibitors of the following formula:

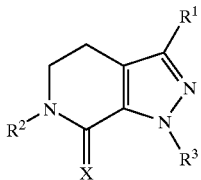

wherein X can be oxygen and $R^2$ and $R^3$ can be a number of substituents including heterocycle, heterocycloalkyl, and phenyl. However, the presently claimed compounds do not correspond to the compounds of WO96/12720. Furthermore, WO96/12720 does not suggest Factor Xa inhibition.

WO98/52948 depicts inhibitors of ceramide-mediated signal transduction. One of the types of inhibitors described is of the following formula:

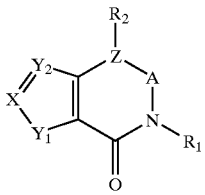

wherein $Y_1$ can be N—$R_6$, $R_6$ can be unsubstituted arylalkyl or unsubstituted heterocyclic-alkyl and $R_1$ can be a substituted aryl group. WO98/52948 does not mention factor Xa inhibition or show compounds like those of the present invention.

U.S. Pat. Nos. 3,365,459, 3,340,269, and 3,423,414 illustrate anti-inflammatory inhibitors of the following formula:

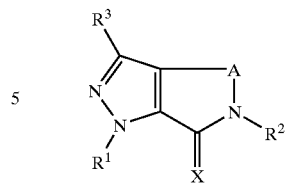

wherein A is 2–3 carbon atoms, X can be O, and $R^1$ and $R^3$ can be substituted or unsubstituted aromatic groups. Neither of these patents, however, exemplify compounds of the present invention.

WO00/39131 describes heterobicyclic factor Xa inhibitors of which the following formula is an example:

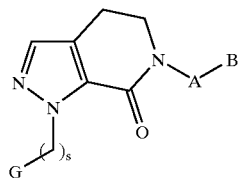

wherein G can be a substituted phenyl, s can be 0, A can be phenyl, and B can be a substituted phenyl or imidazolyl.

WO01/19798 describes factor Xa inhibitors of the following formula:

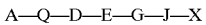

A—Q—D—E—G—J—X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursoR is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel 1,4,5,6-tetrahydropyrazolo-[3,4-c]-pyridin-7-ones that are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide a novel method of treating a patient in need of thromboembolic disorder treatment, comprising: administering a compound of the present invention or a pharmaceutically acceptable salt form thereof in an amount effective to treat a thromboembolic disorder.

It is another object of the present invention to provide a novel method, comprising: administering a compound of the present invention or a pharmaceutically acceptable salt form thereof in an amount effective to treat a thromboembolic disorder.

It is another object of the present invention to provide novel compounds for use in therapy.

It is another object of the present invention to provide the use of novel compounds for the manufacture of a medicament for the treatment of a thromboembolic disorder.

These and other objects, which will become apparent during the following detailed description, have been achieved by the inventors' discovery that compounds of the following formula:

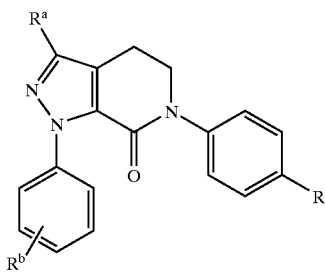

or pharmaceutically acceptable salt or prodrug forms thereof, are effective factor Xa inhibitors.

DETAILED DESCRIPTION OF PREFERRED EMBODIMENTS

Thus, in an embodiment, the present invention provides a novel compound of formula Ia or Ib:

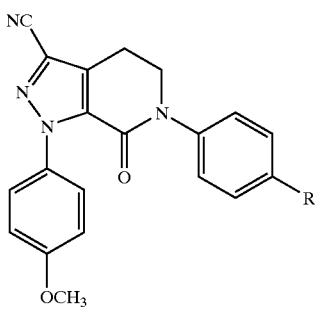

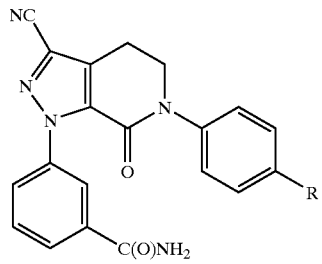

wherein:
R is 2-$R^1$-phenyl or 2-$R^1$-imidazol-1-yl;
$R^1$ is selected from $CH_3$, $CH_2$—$NH_2$, $CH_2$—$NHCH_3$, $CH_2$—$NH(CH_2CH_3)$, $CH_2$—$NH(CH_2CH_2OH)$, $CH_2$—$NH(CH_2CH_2CH_3)$, $CH_2$—$NH(CH(CH_3)_2)$, $CH_2$—$NHC(CH_3)_3$, $CH_2$—$N(CH_3)_2$, $CH_2$—$NCH_3$ $(CH_2CH_3)$, $CH_2$—$NCH_3(CH_2CH_2OH)$, $CH_2$—$NCH_3$ $(CH_2CH_2CH_3)$, $CH_2$—$N(CH_2CH_3)_2$, $CH_2$—NH-pyrrolidinyl, $CH_2$—NH-(3-hydroxy-pyrrolidinyl), $CH_2$—NH-(3-R-hydroxy-pyrrolidinyl), $CH_2$—NH-(3-S-hydroxy-pyrrolidinyl), and $CH_2$—NH-(4-hydroxy-piperidinyl);
alternatively, R is 3-$R^1$-pyridin-4-yl and $R^1$ is $SO_2NH_2$; or a pharmaceutically acceptable salt form thereof.

In a preferred embodiment, the present invention provides a compound wherein the compound is of formula Ia or Ib, R is 2-$R^1$-phenyl, and $R^1$ is $CH_2$—N—$(CH_3)_2$.

In another preferred embodiment, the present invention provides a compound wherein the compound is of formula Ia or Ib, R is 2-$R^1$-phenyl, and $R^1$ is $CH_2$—NH-(4-hydroxy-piperidinyl).

In another preferred embodiment, the present invention provides a compound wherein the compound is of formula Ia or Ib, R is 2-$R^1$-phenyl, and $R^1$ is $CH_2$—NH-(3-hydroxy-pyrrolidinyl).

In another preferred embodiment, the present invention provides a compound wherein the compound is of formula Ia or Ib, R is 2-$R^1$-phenyl, and $R^1$ is $CH_2$—$NCH_3$ $(CH_2CH_2OH)$.

In another preferred embodiment, the present invention provides a compound wherein the compound is of formula Ia or Ib, R is 2-$R^1$-phenyl, and $R^1$ is $CH_2$—NH $(CH_2CH_2OH)$.

In another preferred embodiment, the present invention provides a compound wherein the compound is of formula Ia, R is 2-$R^1$-imidazol-1-yl, and $R^1$ is $CH_2$—NH $(CH_2CH_2CH_3)$.

In another embodiment, the present invention provides a novel compound of formula IIa or IIb:

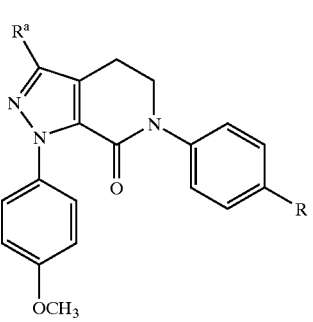

-continued

IIb

[Chemical structure: pyrazolo-pyridinone bicyclic core with R$^a$ substituent on pyrazole, phenyl group with C(O)NH$_2$ attached to one nitrogen, and a para-R-substituted phenyl attached to the other nitrogen via C=O]

wherein:
R$^a$ is selected from CF$_3$, C(O)NH$_2$, C(O)N(CH$_3$)$_2$, and S(O)$_2$CH$_3$:
R is 2-R$^1$-imidazol-1-yl;
R$^1$ is selected from CH$_3$, CH$_2$—NH$_2$, CH$_2$—NHCH$_3$, CH$_2$—NH(CH$_2$CH$_3$), CH$_2$—NH(CH$_2$CH$_2$OH), CH$_2$—NH(CH$_2$CH$_2$CH$_3$), CH$_2$—NH(CH(CH$_3$)$_2$), CH$_2$—NHC(CH$_3$)$_3$, CH$_2$—N(CH$_3$)$_2$, CH$_2$—NCH$_3$(CH$_2$CH$_3$), CH$_2$—NCH$_3$(CH$_2$CH$_2$OH), CH$_2$—NCH$_3$(CH$_2$CH$_2$CH$_3$), CH$_2$—N(CH$_2$CH$_3$)$_2$, CH$_2$—NH-cyclopropyl, CH$_2$—N(CH$_3$)-cyclopropyl, CH$_2$—NH-cyclopentyl, CH$_2$—NH-pyrrolidinyl, CH$_2$—NH-(3-hydroxy-pyrrolidinyl), CH$_2$—NH-(3-R-hydroxy-pyrrolidinyl), CH$_2$—NH-(3-S-hydroxy-pyrrolidinyl), CH$_2$—NH-(2-(pyridin-3-ylmethyl)-pyrrolidinyl), and CH$_2$—NH-(4-hydroxy-piperidinyl);
alternatively, R is 3-R$^1$-pyridin-4-yl and R$^1$ is SO$_2$NH$_2$; or a pharmaceutically acceptable salt form thereof.

In another preferred embodiment, the present invention provides a compound wherein the compound is of formula IIb, R$^a$ is CF$_3$, R is 2-R$^1$-imidazol-1-yl, and R$^1$ is CH$_2$—N(CH$_3$)$_2$.

In another preferred embodiment, the present invention provides a compound wherein the compound is of formula IIb, R$^a$ is CF$_3$, R is 2-R$^1$-imidazol-1-yl, and R$^1$ is CH$_2$—NH-pyrrolidinyl.

In another preferred embodiment, the present invention provides a compound wherein the compound is of formula IIb, R$^a$ is CF$_3$, R is 2-R$^1$-imidazol-1-yl, and R$^1$ is CH$_2$—NH-(3-R-hydroxy-pyrrolidinyl).

In another preferred embodiment, the present invention provides a compound wherein the compound is of formula IIb, R$^a$ is CF$_3$, R is 2-R$^1$-imidazol-1-yl, and R$^1$ is CH$_3$.

In another preferred embodiment, the present invention provides a compound wherein the compound is of formula IIb, R$^a$ is CF$_3$, R is 2-R$^1$-imidazol-1-yl, and R$^1$ is CH$_2$—NHCH$_3$.

In another preferred embodiment, the present invention provides a compound wherein the compound is of formula IIb, R$^a$ is CF$_3$, R is 2-R$^1$-imidazol-1-yl, and R$^1$ is CH$_2$—NH-(4-hydroxy-piperidinyl).

In another preferred embodiment, the present invention provides a compound wherein the compound is of formula IIb, R$^a$ is CF$_3$, R is 2-R$^1$-imidazol-1-yl, and R$^1$ is CH$_2$—NH-(3-S-hydroxy-pyrrolidinyl).

In another preferred embodiment, the present invention provides a compound wherein the compound is of formula IIb, R$^a$ is C(O)NH$_2$, R is 3-R$^1$-pyridin-4-yl, and R$^1$ is SO$_2$NH$_2$.

In another preferred embodiment, the present invention provides a compound wherein the compound is of formula IIa, R$^a$ is CF$_3$, R is 2-R$^1$-imidazol-1-yl, and R$^1$ is CH$_2$—NH-(3-hydroxy-pyrrolidinyl).

In another preferred embodiment, the present invention provides a compound wherein the compound is of formula IIa, R$^a$ is CF$_3$, R is 2-R$^1$-imidazol-1-yl, and R$^1$ is CH$_2$—N(CH$_3$)$_2$.

In another preferred embodiment, the present invention provides a compound wherein the compound is of formula IIa, R$^a$ is C(O)NH$_2$, R is 2-R$^1$-imidazol-1-yl, and R$^1$ is CH$_2$—N(CH$_3$)$_2$.

In another preferred embodiment, the present invention provides a compound wherein the compound is of formula IIa, R$^a$ is CF$_3$, R is 2-R$^1$-imidazol-1-yl, and R$^1$ is CH$_2$—NH-pyrrolidinyl.

In another preferred embodiment, the present invention provides a compound wherein the compound is of formula IIa, R$^a$ is C(O)NH$_2$, R is 2-R$^1$-imidazol-1-yl, and R$^1$ is CH$_2$—NH-pyrrolidinyl.

In another preferred embodiment, the present invention provides a compound wherein the compound is of formula IIa, R$^a$ is CF$_3$, R is 2-R$^1$-imidazol-1-yl, and R$^1$ is CH$_2$—NH-(3-R-hydroxy-pyrrolidinyl).

In another preferred embodiment, the present invention provides a compound wherein the compound is of formula IIa, R$^a$ is C(O)NH$_2$, R is 2-R$^1$-imidazol-1-yl, and R$^1$ is CH$_2$—NH-(3-R-hydroxy-pyrrolidinyl).

In another preferred embodiment, the present invention provides a compound wherein the compound is of formula IIa, R$^a$ is CF$_3$, R is 2-R$^1$-imidazol-1-yl, and R$^1$ is CH$_2$—NH-(3-S-hydroxy-pyrrolidinyl).

In another preferred embodiment, the present invention provides a compound wherein the compound is of formula IIa, R$^a$ is C(O)NH$_2$, R is 2-R$^1$-imidazol-1-yl, and R$^1$ is CH$_2$—NH-(3-S-hydroxy-pyrrolidinyl).

In another preferred embodiment, the present invention provides a compound wherein the compound is of formula IIa, R$^a$ is CF$_3$, R is 2-R$^1$-imidazol-1-yl, and R$^1$ is CH$_3$.

In another preferred embodiment, the present invention provides a compound wherein the compound is of formula IIa, R$^a$ is C(O)NH$_2$, R is 2-R$^1$-imidazol-1-yl, and R$^1$ is CH$_3$.

In another preferred embodiment, the present invention provides a compound wherein the compound is of formula IIa, R$^a$ is CF$_3$, R is 2-R$^1$-imidazol-1-yl, and R$^1$ is CH$_2$—NHCH$_3$.

In another preferred embodiment, the present invention provides a compound wherein the compound is of formula IIa, R$^a$ is C(O)NH$_2$, R is 2-R$^1$-imidazol-1-yl, and R$^1$ is CH$_2$—NH(CH$_3$).

In another preferred embodiment, the present invention provides a compound wherein the compound is of formula IIa, R$^a$ is CF$_3$, R is 2-R$^1$-imidazol-1-yl, and R$^1$ is CH$_2$—NH-(4-hydroxy-piperidinyl).

In another preferred embodiment, the present invention provides a compound wherein the compound is of formula IIa, R$^a$ is C(O)NH$_2$, R is 2-R$^1$-imidazol-1-yl, and R$^1$ is CH$_2$—NH-(4-hydroxy-piperidinyl).

In another preferred embodiment, the present invention provides a compound wherein the compound is of formula IIa, R$^a$ is C(O)N(CH$_3$)$_2$, R is 2-R$^1$-imidazol-1-yl, and R$^1$ is CH$_2$—NHCH$_3$.

In another preferred embodiment, the present invention provides a compound wherein the compound is of formula IIa, R$^a$ is C(O)NH$_2$, R is 2-R$^1$-imidazol-1-yl, and R$^1$ is CH$_2$—NHCH$_3$.

In another preferred embodiment, the present invention provides a compound wherein the compound is of formula IIa, R$^a$ is S(O)$_2$CH$_3$, R is 2-R$^1$-imidazol-1-yl, and R$^1$ is CH$_2$—NHCH$_3$.

In another preferred embodiment, the present invention provides a compound wherein the compound is of formula IIa, R$^a$ is C(O)NH$_2$, R is 2-R$^1$-imidazol-1-yl, and R$^1$ is CH$_2$—NHCH$_2$CH$_3$.

In another preferred embodiment, the present invention provides a compound wherein the compound is of formula IIa, $R^a$ is C(O)NH$_2$, R is 2-$R^1$-imidazol-1-yl, and $R^1$ is CH$_2$—NHCH(CH$_3$)$_2$.

In another preferred embodiment, the present invention provides a compound wherein the compound is of formula IIa, $R^a$ is C(O)NH$_2$, R is 2-$R^1$-imidazol-1-yl, and $R^1$ is CH$_2$—NHCH$_2$CH$_2$CH$_3$.

In another preferred embodiment, the present invention provides a compound wherein the compound is of formula IIa, $R^a$ is S(O)$_2$CH$_3$, R is 2-$R^1$-imidazol-1-yl, and $R^1$ is CH$_2$—NHCH$_2$CH$_3$.

In another preferred embodiment, the present invention provides a compound wherein the compound is of formula IIa, $R^a$ is S(O)$_2$CH$_3$, R is 2-$R^1$-imidazol-1-yl, and $R^1$ is CH$_2$—NHCH$_2$CH$_2$CH$_3$.

In another preferred embodiment, the present invention provides a compound wherein the compound is of formula IIa, $R^a$ is S(O)$_2$CH$_3$, R is 2-$R^1$-imidazol-1-yl, and $R^1$ is CH$_2$—NHCH(CH$_3$)$_2$.

In another preferred embodiment, the present invention provides a compound wherein the compound is of formula IIa, $R^a$ is S(O)$_2$CH$_3$, R is 2-$R^1$-imidazol-1-yl, and $R^1$ is CH$_2$—NH-cyclopropyl.

In another preferred embodiment, the present invention provides a compound wherein the compound is of formula IIa, $R^a$ is C(O)NH$_2$, R is 2-$R^1$-imidazol-1-yl, and $R^1$ is CH$_2$—NH-cyclopropyl.

In another preferred embodiment, the present invention provides a compound wherein the compound is of formula IIa, $R^a$ is C(O)NH$_2$, R is 2-$R^1$-imidazol-1-yl, and $R^1$ is CH$_2$—N(CH$_3$)-cyclopropyl.

In another preferred embodiment, the present invention provides a compound wherein the compound is of formula IIa, $R^a$ is C(O)NH$_2$, R is 2-$R^1$-imidazol-1-yl, and $R^1$ is CH$_2$—NH-cyclopentyl.

In another embodiment, the present invention provides a novel compound of formula IIIa or IIIb:

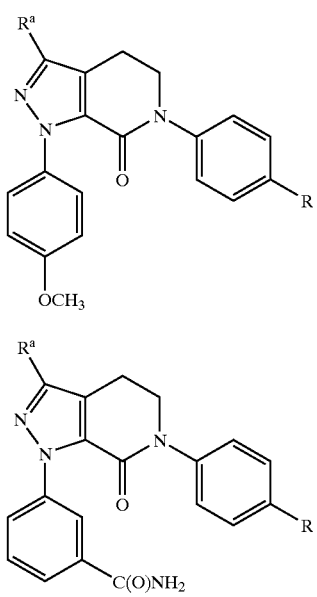

wherein:
$R^a$ is CF$_3$ or C(O)NH$_2$;
R is 2-$R^1$-phenyl;
$R^1$ is selected from CH$_3$, CH$_2$—NH(CH$_2$CH$_3$), CH$_2$—NH(CH$_2$CH$_2$OH), CH$_2$—NH(CH$_2$CH$_2$CH$_3$), CH$_2$—NH(CH(CH$_3$)$_2$), CH$_2$—NHC(CH$_3$)$_3$, CH$_2$—NCH$_3$ (CH$_2$CH$_3$), CH$_2$—NCH$_3$(CH$_2$CH$_2$OH), CH$_2$—NCH$_3$ (CH$_2$CH$_2$CH$_3$), CH$_2$—N(CH$_2$CH$_3$)$_2$, CH$_2$—NH-pyrrolidinyl, CH$_2$—NH-(3-hydroxy-pyrrolidinyl), CH$_2$—NH-(3-R-hydroxy-pyrrolidinyl), CH$_2$—NH-(3-S-hydroxy-pyrrolidinyl), CH$_2$—NH-(2-(pyridin-3-ylmethyl)-pyrrolidinyl), and CH$_2$—NH-(4-hydroxy-piperidinyl);
alternatively, R is 3-$R^1$-pyridin-4-yl and $R^1$ is SO$_2$NH$_2$; or a pharmaceutically acceptable salt form thereof.

In another preferred embodiment, the present invention provides a compound wherein the compound is of formula IIIb, $R^a$ is CF$_3$, R is 2-$R^1$-phenyl, and $R^1$ is CH$_2$—NH-(4-hydroxy-piperidinyl).

In another preferred embodiment, the present invention provides a compound wherein the compound is of formula IIIb, $R^a$ is CF$_3$, R is 2-$R^1$-phenyl, and $R^1$ is CH$_2$—NCH$_3$ (CH$_2$CH$_3$).

In another preferred embodiment, the present invention provides a compound wherein the compound is of formula IIIb, $R^a$ is CF$_3$, R is 2-$R^1$-phenyl, and $R^1$ is CH$_2$—N (CH$_2$CH$_3$)$_2$.

In another preferred embodiment, the present invention provides a compound wherein the compound is of formula IIIb, $R^a$ is CF$_3$, R is 2-$R^1$-phenyl, and $R^1$ is CH$_2$—NH-pyrrolidinyl.

In another preferred embodiment, the present invention provides a compound wherein the compound is of formula IIIb, $R^a$ is CF$_3$, R is 2-$R^1$-phenyl and $R^1$ is CH$_2$—NH-(3-R-hydroxy-pyrrolidinyl).

In another preferred embodiment, the present invention provides a compound wherein the compound is of formula IIIb, $R^a$ is CF$_3$, R is 2-$R^1$-phenyl and $R^1$ is CH$_2$—NH-(3-S-hydroxy-pyrrolidinyl).

In another preferred embodiment, the present invention provides a compound wherein the compound is of formula IIIb, $R^a$ is CF$_3$, R is 2-$R^1$-phenyl, and $R^1$ is CH$_2$—NCH$_3$ (CH$_2$CH$_2$CH$_3$).

In another preferred embodiment, the present invention provides a compound wherein the compound is of formula IIIb, $R^a$ is CF$_3$, R is 2-$R^1$-phenyl, and $R^1$ is CH$_2$—NHC (CH$_3$)$_3$.

In another preferred embodiment, the present invention provides a compound wherein the compound is of formula IIIb, $R^a$ is CF$_3$, R is 2-$R^1$-phenyl, and $R^1$ is CH$_2$—NH-(2-(pyridin-3-ylmethyl)-pyrrolidinyl).

In another preferred embodiment, the present invention provides a compound wherein the compound is of formula IIIa, $R^a$ is CF$_3$, R is 2-$R^1$-phenyl, and $R^1$ is CH$_2$—NH-(3-R-hydroxy-pyrrolidinyl).

In another preferred embodiment, the present invention provides a compound wherein the compound is of formula IIIa, $R^a$ is CF$_3$, R is 2-$R^1$-phenyl, and $R^1$ is CH$_2$—NH-(3-hydroxy-pyrrolidinyl).

In another preferred embodiment, the present invention provides a compound wherein the compound is of formula IIIa, $R^a$ is CF$_3$, R is 2-$R^1$-phenyl and $R^1$ is CH$_2$—NH-(3-S-hydroxy-pyrrolidinyl).

In another preferred embodiment, the present invention provides a compound wherein the compound is of formula IIIa, $R^a$ is CF$_3$, R is 2-$R^1$-phenyl, and $R^1$ is CH$_2$—NH-(4-hydroxy-piperidinyl).

In another preferred embodiment, the present invention provides a compound wherein the compound is of formula IIIa, $R^a$ is C(O)NH$_2$, R is 2-$R^1$-phenyl, and $R^1$ is CH$_2$—NH-(3-R-hydroxy-pyrrolidinyl).

In another preferred embodiment, the present invention provides a compound wherein the compound is of formula IIIa, $R^a$ is $CF_3$, R is 2-$R^1$-phenyl and $R^1$ is $CH_2$—NH-(3-S-hydroxy-pyrrolidinyl).

In another preferred embodiment, the present invention provides a compound wherein the compound is of formula IIIa, $R^a$ is $C(O)NH_2$, R is 2-$R^1$-phenyl, and $R^1$ is $CH_2$—NH-(4-hydroxy-piperidinyl).

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention provides the use of a compound of the present invention as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Utility

The compounds of this invention are useful as anticoagulants for the treatment or prevention of thromboembolic disorders in mammals. In general, a thromboembolic disorder is a circulatory disease caused by blood clots (i.e., diseases involving platelet activation and/or platelet aggregation). The term "thromboembolic disorders" as used herein includes arterial cardiovascular thromboembolic disorders, venous cardiovascular thromboembolic disorders, arterial cerebrovascular thromboembolic disorders, and venous cerebrovascular thromboembolic disorders. The term "thromboembolic disorders" as used herein includes specific disorders selected from, but not limited to, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous translumianl coronary angioplasty). The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine and clopidogrel, including pharmaceutically acceptable salts or prodrugs thereof. Ticlopidine and clopidogrel are also preferred compounds since they are known to be gentle on the gastro-intestinal tract in use. Still other suitable platelet inhibitory agents include IIb/IIIa antagonists, including tirofiban, eptifibatide, and abciximab, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics (or fibrinolytic) agents (or thrombolytics or fibrinolytics), as used herein, denotes agents that lyse blood clots (thrombi). Such agents include tissue plasminogen activator and modified forms thereof, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

1-(4-methoxyphenyl)-6-{2'-[(methylamino)methyl]-1,1'-biphenyl-4-yl}-7-oxo-4,5,6,7-tetrahydro-1H-pyrazolo[3,4-c]pyridine-3-carboxamide Part A:

p-Anisidine (16 g, 0.129 mol) in conc. HCl (40 mL) and 100 mL $H_2O$ was cooled to −5° C. and sodium nitrite (9.4 g, 0.136 mol) in $H_2O$ (60 mL) was added. The diazotization was stirred cold for 20 min and a mixture of ethyl chloroacetoacetate (22 g, 0.133 mol), ethanol (100 mL), sodium acetate (32 g, 0.389 mol), and $H_2O$ (400 mL) was added. The reaction was allowed to warm to room temperature and stirred for 2 h. The product precipitated as a black solid (30 g), and was collected and dried in vacuo. $^1$H NMR (CDCl$_3$) δ: 8.28 (s, 1H), 7.18 (d, j=9.1 Hz, 2H), 6.90 (d, j=9.2 Hz, 2H), 4.41 (q, j=7 Hz, 2H), 3.80 (s, 3H), 1.42 (t, j=7.3 Hz, 3H) ppm.

Part B:

The product of part A (30 g, 0.117 mol) was stirred with iodomorpholine (29.9 g, 0.078 mol) and triethylamine (74 mL, 0.53 mol) at reflux in toluene (400 mL) for 24 h. The reaction was cooled, washed with water, and dried (Na$_2$SO$_4$). Purification by silica gel chromatography using 1:1 hexane/ethyl acetate as eluent afforded the morpholine intermediate. Treatment of the morpholine intermediate with trifluoroacetic acid (50 mL) in CH$_2$Cl$_2$ (500 mL) for 24 h followed by washing with water and drying (Na$_2$SO$_4$) afforded 28.8 g (71%)of the ester-iodo intermediate B; Mass Spec (M+H)$^+$ 517.9.

Part C:

To a solution of ammonium chloride (1 g, 19 mmol) in xylenes (250 mL) was added trimethylaluminum (2M, heptanes, 19.3 mL, 38 mmol), which was stirred for 20 min. The product from part B (9.1 g, 17.6 mmol) was then added and the reaction was heated to reflux for 3 h. The reaction was cooled to 0° C., quenched with HCl, extracted with ethylacetate, washed with brine and dried (Na$_2$SO$_4$). The crude mixture was treated with 30% H$_2$O$_2$ (70 mL), 10% NaOH (150 mL) in CH$_2$Cl$_2$ (400 mL) for 24 h. Extraction of the aqueous layer with CH$_2$Cl$_{21}$ washing with water and drying (Na$_2$SO$_4$) afforded 6.18 g of the desired amide (72%); $^1$H NMR (CDCl$_3$) δ: 7.68 (d, j=8.5 Hz, 2H), 7.47 (d, j=8.8 Hz, 2H), 7.09 (d, j=8.8 Hz, 2H), 6.95 (d, j=8.8 Hz, 2H), 6.86 (s, 1H), 5.70 (s, 1H), 4.10 (t, j=6.6 Hz, 2H), 3.82 (s, 3H), 3.17 (t, j=6.6, 2H) ppm.

Part D:

The amide from part C (9.2 g, 19.3 mmol) was placed in a solution of toluene (300 mL), methanol (50 mL) and Na$_2$CO$_3$(2M, 20 mL), with 2-formylphenylboronic acid (4.3 g, 29 mmol). Tetrakistriphenylphosphine palladium (100 mg) was added and the reaction was heated to reflux 24 h. The reaction was cooled to room temperature and the product was filtered off and dried to afford 7.8 g (87%) of a solid. $^1$H NMR (DMSO-d$_6$) δ: 9.91 (s, 1H), 7.94 (m, 1H), 7.77 (m, 2H), 7.62 (t, j=7.7 Hz, 1H), 7.50 (m, 8H), 7.02 (d, j=9.1 Hz, 2H), 4.16 (t, j=6.6 Hz, 2H), 3.80 (s, 3H), 3.26 (t, j=6.6 Hz, 2H) ppm.

Part E:

The aldehyde from part D (0.12 g, 0.25 mmol) was stirred with methylamine hydrochloride (34 mg, 0.52 mmol) in 1:1 THF/MeOH (5 mL) for 15 min. ZnCl$_2$ 0.5M in THF (0.25 mL, 0.13 mmol) and sodium cyanoborohydride (16 mg, 0.25 mmol) were added. The reaction was stirred 24 h. The solvents were removed and the residue extracted with ethylacetate, washed with brine, and dried (MgSO$_4$). Purification by HPLC and freeze-drying afforded 70 mg (45%) of the desired product. $^1$H NMR (DMSO-d$_6$) δ: 8.81 (s, 2H), 7.76 (s, 1H), 7.62 (m, 1H), 7.53 (m, 6H), 7.37 (d, j=5.9 Hz, 2H), 7.33 (m, 1H), 7.03 (d, j=8.8 Hz, 2H), 4.12 (m, 4H), 3.80 (s, 3H), 3.26 (t, j=6.2 Hz, 2H), 2.50 (3H, S) ppm; HRMS (M+H)$^+$ for C$_{28}$H$_{28}$N$_5$O$_3$ 482.2185; Elemental Analysis for C$_{28}$H$_{27}$N$_5$O$_3$ (TFA) 1.2 calc'd C, 59.05; H, 4.60; N, 11.33. found C, 58.66; H, 4.59; N, 11.22.

Example 2

6-(2'-{[(3S)-3-hydroxy-1-pyrrolidinyl]methyl}-1,1'-biphenyl-4-yl)-1-(4-methoxyphenyl)-7-oxo-4,5,6,7-tetrahydro-1H-pyrazolo[3,4-c]pyridine-3-carboxamide The title compound was prepared following the protocols for Example 1. $^1$H NMR (DMSO-d$_6$) δ: 7.78 (s, 2H), 7.53 (m, 6H), 7.39 (d, j=8.4 Hz, 2H), 7.34 (m, 1H), 7.02 (d, j=7 Hz, 2H), 4.49 (d, j=5.50 Hz, 1H), 4.38 (m, 1H), 4.30 (m, 1H), 4.14 (t, j=6.3 Hz, 2H), 3.81 (s, 3H), 3.50 (m, 2H), 3.26 (t, j=6.2 Hz, 2H), 3.2–2.85 (m, 3H), 2.1–1.85 (m, 3H) ppm; HRMS (M+H)$^+$ for C$_{31}$H$_{32}$N$_5$O$_4$ 538.2456; Elemental Analysis calc'd for C$_{31}$H$_{31}$N$_5$O$_4$(TFA) 1.3 (H$_2$O) 0.1: C, 58.69; H, 4.76; N, 10.18. found C, 58.61; H, 4.56; N, 10.10.

Example 3

6-{2'-[(4-hydroxy-1-piperidinyl)methyl]-1,1'-biphenyl-4-yl}-1-(4-methoxyphenyl)-7-oxo-4,5,6,7-tetrahydro-1H-pyrazolo[3,4-c]pyridine-3-carboxamide The title compound was prepared following the protocols for Example 1. $^1$H NMR (DMSO-d$_6$) δ: 9.05 (m, 1H), 7.75 (s, 2H), 7.54 (m, 6H), 7.39 (m, 3H), 7.10 (m, 4H), 4.34 (m, 2H), 4.15 (t, j=6.2 Hz, 2H), 3.81 (s, 3H), 3.50 (m, 1H), 3.26 (t, j=6.6 Hz, 2H), 3.05 (m, 1H), 2.85 (m, 2H), 1.75 (m, 2H), 1.55 (m, 2H) ppm; HRMS (M+H)$^+$ for C$_{32}$H$_{34}$N$_5$O$_4$ 522.2619; Analysis for C$_{32}$H$_{33}$N$_5$O$_4$ (TFA) 1.2 (H$_2$O) 1.2 calc'd C, 58.19; H; 5.19; N, 9.86. found C, 58.31; H, 4.88; N, 9.85.

Example 4

6-{4-[3-(aminosulfonyl)-4-pyridinyl]phenyl}-1-(4-methoxyphenyl)-7-oxo-4,5,6,7-tetrahydro-1H-pyrazolo[3,4-c]pyridine-3-carboxamide Part A:

To the iodoester product from Example 1 (part B) (0.24 g, 0.47 mmol), bis-pinacolatodiboron (0.13 g, 0.5 mmol), potassium acetate (0.14 g, 1.4 mmol), and PdCl$_2$(dppf) (25 mg) was added DMF (5 mL). The mixture was heated to 80° C. for 2 h, cooled to room temperature and 3-t-butylsulfonamide-4-iodo-pyridine (0.32 g, 0.9 mmol), PdCl$_2$ (dppf), and 2M Na$_2$CO$_3$ (0.7 mL) were added. The reaction was heated to 80° C. for 24 h. The reaction was cooled, extracted with ethylacetate, washed with brine, and dried (MgSO$_4$). The crude was purified via silica gel column chromatography using ethylacetate:hexane (6:4) as eluent to afford pure product. Mass Spec (M−H) 602.2.

Part B:

To ester from part A was added MeOH (30 mL), NH$_4$OH (15 mL), and NH$_4$Cl (0.5 g) and the reaction was stirred for 72 h. The reaction was concentrated and the residue was treated with TFA (20 mL) for 15 min. The reaction mixture was concentrated and the crude material purified via HPLC and freeze-dried to afford the title compound 90 mg (30%): $^1$H NMR (DMSO-d$_6$) δ: 9.15 (s, 1H), 8.79 (d, j=4.7 Hz, 1H), 7.75 (s, 1H), 7.64 (s, 2H), 7.53–7.40 (m, 8H), 7.02 (d, j=8.8 Hz, 2H), 4.15 (t, j=6.6 Hz, 2H), 3.8 (3H, s), 3.25 (t, j=6.6 Hz, 2H) ppm; HRMS (M+H)$^+$ for C$_{25}$H$_{23}$N$_6$O$_5$S 519.1462; Elemental Analysis calc'd for C$_{25}$H$_{22}$N$_6$O$_5$S (TFA): C, 51.27; H, 3.67; N, 13.29. found C, 50.97; H, 3.73; N, 13.22.

Example 5

6-(4-{2-[(dimethylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide Part A:

To the iodoester product from Example 1 (part B) (0.47 g, 0.9 mmol) in DMSO (7 mL) was added 2-dimethylaminomethyl-imidazole (0.136 g, 1 mmol), 1,10-phenanthroline (8 mg) K$_2$CO$_3$ (0.138 g, 1 mmol), and CuI (8.6 mg, 0.045 mmol), and the reaction was heated to 130° C. for 24 h. The reaction was cooled, diluted with ethyl acetate, washed with dilute NH$_4$OH, and dried (MgSO$_4$). Purification on silica gel using 0–10% MeOH/CH$_2$Cl$_2$ as eluent afforded the desired imidazole ester intermediate; Mass Spec (M+H)$^+$ 515.2.

Part B:

The imidazole ester from part A was placed in MeOH (20 mL) with NH$_4$OH (5 mL) and NH$_4$Cl (100 mg) and stirred for 24 h. The reaction was concentrated and the residue was purified by HPLC and freeze-dried to afford the title compound 55 mg (10%). $^1$H NMR (DMSO-d$_6$) δ: 7.77 (s, 1H), 7.59 (m, 8H), 7.24 (d, j=1.1 Hz, 1H), 7.02 (d, j=8.8 Hz, 2H), 4.43 (s, 2H), 4.13 (t, j=6.6 Hz, 2H), 3.81 (s, 3H), 3.27 (t, j=6.6 Hz, 2H), 2.80 (s, 6H) ppm; HRMS (M+H)$^+$ for C$_{26}$H$_{28}$N$_7$O$_3$ 486.2253; Elemental Analysis for C$_{26}$H$_{27}$N$_7$O$_3$ (TFA) 2.5 (H2O) 1.4: C, 46.79; H, 4.09; N, 12.32. found C, 46.65; H, 4.40; N, 12.71.

Example 6

1-(4-methoxyphenyl)-6-[4-(2-methyl-1H-imidazol-1-yl)phenyl]-7-oxo-4,5,6,7-tetrahydro-1H-pyrazolo[3,4-c]pyridine-3-carboxamide The title compound was prepared via an Ullman coupling procedure using 2-methyl-imidazole, potassium carbonate, and cat. CuI together with the intermediate product obtained in part B of Example 1 in DMSO at 130° C. for 24 h. Conversion to the 3-carboxamide was then done as per conditions outlined in Example 1. Reverse phase HPLC purification afforded pure title compound. $^1$H NMR (DMSO-d$_6$) δ: 7.87 (d, =1.8 Hz, 1H), 7.76 (d, j=2.2 Hz, 2H), 7.64 (s, 4H), 7.53 (d, j=9.1 Hz, 2H), 7.48 (m, 1H), 7.02 (d, j=9.2 Hz, 2H), 4.15 (t, j=6.6 Hz, 2H), 3.81 (s, 3H), 3.27 (t, j=6.6 Hz, 2H), 2.51 (s, 3H) ppm; HRMS for C$_{24}$H$_{23}$N$_6$O$_3$ 443.1833; Elemental Analysis Calc'd for C$_{24}$H$_{22}$N$_6$O$_3$ (TFA) 1.4 (H$_2$O): C, 51.91; H, 4.13; N, 13.55. found C, 51.97; H, 3.98, N, 13.43.

Example 7

6-{2'-[N,N-dimethylaminomethyl]-1,1'-biphenyl-4-yl}-1-(4-methoxyphenyl)-7-oxo-4,5,6,7-tetrahydro-1H-pyrazolo[3,4-c]pyridine-3-carbonitrile Part A:

To a solution of DMF (4.28 mL, 55.3 mmol) and acetonitrile (150 mL) at 0° C. was added oxalyl chloride (3.99 mL, 46.1 mmol). The reaction mixture was stirred until all gas evolution had stopped. The amide product from Example 1 (part C, 9.0 g, 18.4 mmol) was added and stirred until a homogenous mixture had formed. Pyridine (7.45 mL, 92.2 mmol) was added and the reaction was warmed to room temperature and stirred for 2 h. The reaction was quenched with 1N HCl, extracted with ether, washed with brine, and dried (Na$_2$SO$_4$) to afford 6.54 g (75%) of the 3-pyrazole nitrile intermediate. $^1$H NMR (CDCl$_3$) δ: 7.70 (d, j=8.8 Hz, 2H), 7.45 (d, j=9.2 Hz, 2H), 7.05 (d, j=8.8 Hz, 2H), 6.92 (d, j=8.8 Hz, 2H), 4.13 (t, j=6.6 Hz, 2H), 3.83 (s, 3H), 3.17 (t, j=6.6 Hz, 2H) ppm; Mass Spec (M+H)$^+$ 470.9.

Part B:

The 3-pyrazole nitrile intermediate (6.5 g, 13.8 mmol) was placed in a solution of toluene (200 mL), methanol (50 mL), and Na$_2$CO$_3$ (2M, 14 mL) with 2-formylphenyl boronic acid (3.1 g, 20.7 mmol), and the mixture was degassed with N$_2$ for 15 min. Tetrakistriphenylphosphine palladium (75 mg) was added and the reaction was heated to reflux 24 h. The reaction was cooled to room temperature quenched with water, extracted with ethyl acetate, washed with brine, and dried (Na$_2$SO$_4$). Purification by silica gel chromatography using 0%–100% ethyl acetate/hexane gradient as eluent afforded 5.32 g (86%) of the aldehyde intermediate. $^1$H NMR (CDCl$_3$) δ: 9.99 (s, 1H), 8.02 (dd, j=1.1 Hz, 7.7 Hz, 1H), 7.67–7.62 (m, 1H), 7.54–7.36 (m, 8H), 6.95 (d, j=8.8 Hz, 2H), 4.24 (t, j=6.6 Hz, 2H), 3.83 (s, 3H), 3.22 (t, j=6.6 Hz, 2H) ppm.

Part C:

The aldehyde intermediate (0.0808 g, 0.18 mmol) was stirred with dimethylamine hydrochloride (29 mg, 0.36 mmol) in 1:1 THF/MeOH (5 mL) for 15 min. $ZnCl_2$ 0.5M in THF (0.18 mL, 0.09 mmol) and sodium cyanoborohydride (11 mg, 0.18 mmol) were added. The reaction was stirred 24 h. The solvents were removed and the residue extracted with ethyl acetate, washed with brine, and dried ($Na_2SO_4$). Purification by HPLC and freeze-drying afforded 39 mg (45%) of the desired product. $^1$H NMR ($CDCl_3$) δ: 7.73–7.70 (m, 1H), 7.53–7.41 (m, 6H), 7.31–7.25 (m, 3H), 6.96 (d, j=9.2 Hz, 2H), 4.30 (s, 2H), 4.24 (t, j=6.6 Hz, 2H), 3.84 (s, 3H), 3.23 (t, j=6.6 Hz, 2H), 2.57 (s, 6H) ppm; Mass Spec $(M+H)^+$ 478.6.

Example 8

6-{2'-[(4-hydroxy-1-piperidinyl)methyl]-1,1'-biphenyl-4-yl}-1-(4-methoxyphenyl)-7-oxo-4,5,6,7-tetrahydro-1H-pyrazolo[3,4-c]pyridine-3-carbonitrile The title compound was obtained using 4-hydroxy-1-piperidine via the reductive amination and 3-carbonitrile procedures outlined for Example 7. $^1$H NMR ($CDCl_3$) δ: 7.75–7.70 (m, 1H), 7.49–7.40 (m, 6H), 7.29–7.24 (m, 3H), 6.97–6.93 (m, 2H), 4.28–4.23 (m, 5H), 4.07 (bs, 1H), 3.90–3.77 (m, 2H), 3.83 (s, 3H), 3.35–3.14 (m, 4H), 2.80–2.76 (m, 1H), 2.10 (bt, j=13.2 Hz, 1H), 1.88 (bs, 1H), 1.69 (bd, j=13.9 Hz, 1H) ppm; Mass Spec $(M+H)^+$ 534.4. Elemental Analysis calc'd for $C_{34}H_{32}N_5O_5F_3$(TFA) 1.5 ($H_2O$): C, 59.53; H, 4.85; N, 9.92. found C, 59.30; H, 4.54; N, 10.02.

Example 9

6-(2'-{[(3S)-3-hydroxy-1-pyrrolidinyl]methyl}-1,1'-biphenyl-4-yl)-1-(4-methoxyphenyl)-7-oxo-4,5,6,7-tetrahydro-1H-pyrazolo[3,4-c]pyridine-3-carbonitrile The title compound was obtained using (3S)-3-hydroxy-1-pyrrolidine via the reductive amination and 3-carbonitrile procedures outlined for Example 7. $^1$H NMR (DMSO-$d_6$) δ: 7.74–7.66 (m, 1H), 7.53–7.43 (m, 6H), 4.37–4.28 (m, 3H), 7.00 (d, j=9.1 Hz, 2H), 4.45 (bs, 1H), 4.36–4.33 (m, 1H), 4.26–4.24 (m, 1H), 4.13 (t, j=6.3 Hz, 2H), 3.78 (s, 3H), 3.60–3.30 (m, 2H), 3.14 (t, j=6.6 Hz, 2H), 2.95–2.72 (m, 3H), 2.10–1.97 (m, 1H), 1.97–1.78 (m, 1H), 1.76–1.60 (m, 1H) ppm; Mass Spec $(M+H)^+$ 520.5. Elemental Analysis calc'd for $C_{31}H_{29}N_5O_3F_3$(TFA) 1.5 ($H_2O$) 2.0: C, 59.05; H, 4.96; N, 10.26. found C, 59.17; H, 4.96; N, 10.28.

Example 10

6-(2'-{[(2-hydroxyethyl)(methyl)amino]methyl}-1,1'-biphenyl-4-yl)-1-(4-methoxyphenyl)-7-oxo-4,5,6,7-tetrahydro-1H-pyrazolo[3,4-c]pyridine-3-carbonitrile The title compound was obtained using 2-hydroxyethylmethylamine via the reductive amination and 3-carbonitrile procedures outlined for Example 7. $^1$H NMR ($CDCl_3$) δ: 7.78–7.74 (m, 1H), 7.51–7.41 (m, 6H), 7.32–7.26 (m, 3H), 6.95 (d, j=9.2 Hz, 2H), 4.48–4.23 (m, 2H), 4.23 (t, j=6.6 Hz, 2H), 3.84–3.81 (m, 2H), 3.84 (s, 3H), 3.22 (t, j=6.6 Hz, 2H), 3.18–2.90 (m, 1H), 2.88–2.64 (m, 1H), 2.63 (s, 3H) ppm; Mass Spec $(M+H)^+$ 508.5. Elemental Analysis calc'd for $C_{30}H_{29}N_5O_3F_3$(TFA) 1.7 ($H_2O$): C, 57.05; H, 4.64; N, 9.96; found C, 57.15; H, 4.49; N, 10.18.

Example 11

6-(2'-{[(2-hydroxyethyl)amino]methyl}-1,1'-biphenyl-4-yl)-1-(4-methoxyphenyl)-7-oxo-4,5,6,7-tetrahydro-1H-pyrazolo[3,4-c]pyridine-3-carbonitrile The title compound was obtained using 2-hydroxyethylamine via the reductive amination and 3-carbonitrile procedure outlined for Example 7. $^1$H NMR ($CDCl_3$) δ: 7.56 (t, j=7.3 Hz, 1H), 7.50–7.38 (m, 6H), 7.34–7.29 (m, 3H), 6.94 (d, j=8.8 Hz, 2H), 4.23–4.16 (m, 4H), 3.83 (s, 3H), 3.65 (s, 2H), 3.56 (bs, 2H), 3.21 (t, j=6.6 Hz, 2H), 2.80 (bs, 1H) ppm; Mass Spec $(M+H)^+$ 494.3.

Example 12

6-(4-{2-[(dimethylamino)methyl]-1H-imidazol-1-yl}phenyl)-1-(4-methoxyphenyl)-3-(trifluoromethyl)-1,4,5,6-tetrahydro-7H-pyrazolo[3,4-c]pyridin-7-one Part A:

Trifluoromethyl-trione (10.0 g, 24.3 mmol) and 4-methoxyhydrazine hydrochloride (4.28 g, 24.3 mmol) were dissolved in HCl (1N, 200 mL) and methanol (400 mL) and refluxed overnight. The reaction was cooled to room temperature, quenched with water, extracted with ethyl acetate, washed with brine, and dried ($Na_2SO_4$). Purification by silica gel chromatography using 0%–100% ethyl acetate/hexane gradient as eluent afforded the desired trifluoromethylpyrazole intermediate 9.28 g (74%); $^1$H NMR ($CDCl_3$) δ: 7.69 (d, j=9.4 Hz, 2H), 7.45 (d, j=8.8 Hz, 2H), 7.06 (d, j=8.8 Hz, 2H), 6.92 (d, j=9.2 Hz, 2H), 4.11 (t, j=6.8 Hz, 2H), 3.81 (s, 3H), 3.15 (t, j=6.5 Hz, 2H) ppm; Mass Spec $(M+H)^+$ 514.3.

Part B:

The trifluoromethylpyrazole intermediate (500 mg, 0.97 mmol), 2-dimethylaminomethylimidazole (146 mg, 1.17 mmol), cesium carbonate (348 mg, 1.07 mmol), and copper iodide (37 mg, 0.20 mmol) were charged to a flask and flushed with $N_2$. DMSO (6 mL) was syringed into the flask and the reaction was heated to 120° C. overnight. The reaction was cooled to room temperature, quenched with water and ammonium hydroxide to pH 12, extracted with ethylacetate, washed with brine, and dried ($Na_2SO_4$). Purification by silica gel chromatography using 0%–100% ethyl acetate/hexane followed by 0%–10% methanol/ethyl acetate as eluents, prep. HPLC, and freeze-dying afforded the desired product 268.6 mg (54%); $^1$H NMR ($CDCl_3$) δ: 7.53–7.43 (m, 4H), 7.37 (d, j=8.5 Hz, 3H), 7.27 (s, 1H), 6.94 (d, j=9.2 Hz, 2H), 4.49 (s, 2H), 4.24 (t, j=6.6 Hz, 2H), 3.82 (s, 3H), 3.22 (t, j=6.4 Hz, 2H), 2.83 (s, 6H) ppm; Mass Spec $(M+H)^+$ 511.5. Elemental Analysis calc'd for $C_{26}H_{25}N_6O_2F_3$(TFA) 2.1 ($H_2O$) 2.0: C, 48.23; H, 3.91; N, 11.17. found C, 48.28; H, 3.58; N, 11.18.

Example 13

1-(4-methoxyphenyl)-6-(4-{2-[(methylamino)methyl]-1H-imidazol-1-yl}phenyl)-3-trifluoromethyl-7-oxo-4,5,6,7-tetrahydro-1H-pyrazolo[3,4-c]pyridine-one Part A:

2-Imidazole carboxyaldehyde (5.0 g, 52.0 mmol) was suspended in 200 mL of methanol. Methylamine (20 mL of 33% solution in methanol) was added. After stirring for 15 minutes, $NaBH_4$ (3.95 g, 0.10 mol) was added portion-wise. The reaction mixture was then heated at 50° C. for 2 h under $N_2$. The solvent was removed. The solid was washed with $CH_2Cl_2$ and filtered. The $CH_2Cl_2$ solution was dried over $MgSO_4$, concentrated, and dried under vacuum to give the methylamine as a yellow oil. This oil was dissolved in a 1:1 solution of $CH_2Cl_2$ and THF. To this solution was added $Et_3N$ (7.94 mL, 57.0 mmol) and benzylchloroformate (7.4 mL, 52.0 mmol). The mixture was stirred at room temperature under $N_2$ for 1 h. The solvent was removed and the residue was partitioned between EtOAc and $H_2O$. The EtOAc layer was washed with brine, dried over $MgSO_4$, and concentrated. The mixture was refluxed with 15 mL of TFA for 30 minutes to convert most of the bis-acylated byproduct to the desired product. The TFA was removed. The remaining solid was dissolved in ethyl acetate and washed with saturated aqueous $NaHCO_3$ and brine. The mixture was dried over $MgSO_4$, concentrated, and chromatographed with 1:1 EtOAc/hexane to give 6.56 g off-white solid (51.4% yield). MS (AP$^+$): 246.3, (M+H)$^+$. $^1$HNMR (CDCl$_3$) δ: 7.35 (s, 6H), 6.90 (s, 1H), 5.14 (s, 2H), 4.48 (s, 2H), 3.00 (s, 3H) ppm.

Part B:

To the product of part A, Example 12 (1.17 g, 4.76 mmol) was added the imidazolyl compound prepared above (part A, 1.63 g, 3.18 mmol), CuI (0.12 g, 20%), $K_2CO_3$ (0.66 g, 4.76 mmol), and 1,10-phenanthroline (56 mg, 20%) with 100 mL of DMSO. The mixture was degassed and then heated at 130° C. under $N_2$ for 12 h. The mixture was cooled and aqueous $NH_4OH$ (200 mL of 10% $NH_4OH$) was added. The mixture was filtered through Celite® and washed with EtOAc. The two layers were separated, and the aqueous layer was extracted with EtOAc. The combined EtOAc mixture was washed with brine, dried over $MgSO_4$, concentrated, and chromatographed with EtOAc to give 1.34 g of the desired product (66.9%). MS (ES$^+$): 631.3, (M+H).

Part C:

The above solid was heated with 15 mL of TFA at 80° C. for 1 h. The solvent was removed. The crude product was purified by reverse phase HPLC (C18 reverse phase column, eluted with a $H_2O/CH_3CN$ gradient with 0.05% TFA) to give 0.50 g of the desired product as the TFA salt (25.7%). MS (ES$^+$): 497.5, (M+H)$^+$. $^1$HNMR (CDCl$_3$) δ: 7.32–7.51 (m, 7H), 7.17 (s, 1H), 6.94 (d, 2H), 4.83 (s, 2H), 4.18 (t, 2H), 3.82 (s, 3H), 3.22 (t, 2H), 3.17 (s, 3H) ppm.

Example 14

1-(4-methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxamide Reaction of the product of part A (Example 13) with the pyrazole 3-carboxylate obtained part B (Example 1) afforded the desired 3-carboxy-pyrazole ester intermediate. The ester was hydrogenated with 20% Pd(OH)$_2$ in EtOH then hydrolyzed with concentrated $NH_4OH$ in dioxane to give the desired product. The crude product was purified by reverse phase HPLC (C18 reverse phase column, eluted with a $H_2O/CH_3CN$ gradient with 0.05% TFA) to give the final product as its TFA salt. MS (ES$^+$): 472.3, (M+H)$^+$. $^1$H NMR (CD$_3$OD): δ 7.42–7.61 (m, 7H), 7.22 (s, 1H), 6.99 (d, 2H), 4.30 (s, 2H), 4.19 (t, 2H), 3.82 (s, 3H), 3.35 (t, 2H), 2.73 (s, 3H) ppm. HPLC purity 99.7%. HRMS calc'd for $C_{25}H_{26}N_7O_3$ (M+H)$^+$=472.2097. found 472.2089.

Example 15

3-[4,5,6,7-Tetrahydro-6-[2'-[[N,N-dimethylamino]methyl][1,1'-biphenyl]-4-yl]-3-trifluoromethyl-7-oxo-1H-pyrazolo[3,4-c]pyridin-1-yl]benzamide•TFA Part A:

3-Aminobenzamide (1 g, 7.35 mmol) in conc. HCl (25 mL) was cooled to 0° C. and $NaNO_2$ (0.61 g, 8.8 mmol) in $H_2O$ (5 mL) was added dropwise. The cold reaction mixture was stirred 30 min then $SnCl_2.(H_2O)_2$ in $H_2O$ (10 mL):conc. HCl (10 mL) solution was added. The reaction was stirred at 0° C. for 2.5 h then filtered, washed with hexane, and air-dried. There was obtained 1.37 g of the hydrazine. LRMS (M+H)$^+$ 152 m/z.

3-Amidophenyl hydrazine, prepared above, (15 g, 40 mmol) and trione (22.4 g, 55 mmol) in AcOH (400 mL) were heated at reflux 18 h. The volume was reduced by distillation to 100 mL then $H_2O$ (1 L) was added. The aqueous layer was extracted with EtOAc (4×200 mL). The EtOAc extracts were washed with 1N NaOH (3×100 mL) and brine. This solution was dried (MgSO$_4$) and evaporated to give 19.4 g (37 mmol, 93%) of the desired product. $^1$H NMR (CDCl$_3$) δ: 8.0 (1H, s), 7.9–7.5 (3H, m), 7.7 (2H, d, J=9 Hz), 7.1 (2H, d, J=9 Hz), 6.8—6.8 (1H, broad), 6.4–6.3 (1H, broad), 4.15 (2H, t, J=6 Hz) and 3.2 (2H, t, J=6 Hz) ppm; LRMS (M+Na)$^+$=549 m/z.

Part B:

6-(4-Iodophenyl)-1,4,5,6-tetrahydro-1-(3-amidophenyl)-3-(trifluoromethyl)-7H-pyrazolo[3,4-c]pyridin -7-one (19 g, 36.1 mmol) and 2-formylphenylboronic acid (16.3 g, 108.3 mmol) in dioxane (300 mL) and 2N $K_2CO_3$ (35 mL) were purged by passing a stream of $N_2$ gas through the solution for 15 min. Following this procedure, tetrakis (triphenylphosphine) palladium catalyst (3 g) was added, the $N_2$ atmosphere re-established, and the mixture heated at reflux for 4 h. The reaction was cooled to ambient temperature and 1-chlorobutane (250 mL) and $H_2O$ (500 mL) was added. This mixture was stirred for 5 h, then filtered, washed with $H_2O$ and air-dried to give 18.1 g of crude product. The filter cake was triturated with $CH_2Cl_2$ (200 mL) and filtered to give 8.0 g (16 mmol, 44%) of the desired product; mp: 259.4° C. $^1$H NMR (CDCl$_3$) δ: 10 (1H, s), 8.1–7.45 (8H, m), 7.4 (4H, s), 4.25 (2H, t, J=6 Hz) and 3.2 (2H, t, J=6 Hz) ppm; LRMS (M+H)$^+$=505.3 m/z.

Part C:

A mixture of 3-[4,5,6,7-tetrahydro-6-[2'-[formyl][1,1'-biphenyl]-4-yl]-3-trifluoromethyl-7-oxo-1H-pyrazolo[3,4-c]pyridin-1-yl]benzamide, prepared above, (5.6 g, 10 mmol), 2M dimethylamine in THF (20 mL, 40 mmol), acetic acid (3 g, 50 mmol), and sodium triacetoxyborohydride (8.5 g, 40 mmol) were stirred in THF (250 mL) for 18 h. The reaction was partitioned between EtOAc (250 mL) and 5% $NaHCO_3$ (100 mL). The EtOAc layer was washed with water (3×100 mL) and brine, dried over $K_2CO_3$, and evaporated to give 3.5 g of crude product. This material was decolorized with activated charcoal and recrystallized from AcCN to give 2.78 g (5.2 mmol, 52%, HPLC purity: 98%). The free base was taken up in $CH_2Cl_2$ and excess TFA was added. The solvent was removed in vacuo, suspended in water, and lyophyllized. There was obtained 3.73 g of the TFA salt of the product (5.2 mmol); mp 112.6° C.; $^1$H NMR (CDCl$_3$) δ: 8.1 (1H, s), 7.85 (1H, d, J=7 Hz), 7.8 (1H, d, J=7 Hz), 7.7 (1H, m), 7.6–7.2 (8H, m), 4.3 (2H, s), 4.25 (2H, t, J=6 Hz), 3.25 (2H, t, J=6 Hz) and 2.6 (6H, s) ppm; (HRMS (M+H)$^+$ for $C_{29}H_{27}O_2F_3N_5$: obs. 534.2115, calc. 534.2117.

Example 16

3-[4,5,6,7-Tetrahydro-6-[2'-[[4-hydroxypiperidin-1-yl]methyl][1,1'-biphenyl]-4-yl]-3-trifluoromethyl-7-oxo-1H-pyrazolo[3,4-c]pyridin-1-yl]benzamide•TFA This compound was prepared as described for Example 15 with 4-hydroxypiperidine substituted for N,N-dimethylamine in Part C; $^1$H NMR (CDCl$_3$) δ: 8.1 (1H, s), 7.9–7.1 (11H, m), 4.4–4.2 (4H, m), 4.0 (1H, m), 3.25 (2H, t, J=6 Hz), 3.15 (1H, m), and 2.7 ppm (1H, m); HRMS (M+H)$^+$: 590.2362 m/z.

Example 17

3-[4,5,6,7-Tetrahydro-6-[2'-[[N-ethyl-N-methylamino]methyl][1,1'-biphenyl]-4-yl]-3-trifluoromethyl-7-oxo-1H-pyrazolo[3,4-c]pyridin-1-yl]benzamide•TFA This compound was prepared as described for Example 15 with N-ethyl-N-methyl amine substituted for N,N- dimethylamine in Part C; mp 65.2° C.; $^1$H NMR (CDCl$_3$) δ: 8.1 (s, 1H), 7.9 (1H, d, J=8 Hz), 7.8 (1H, d, J=8 Hz), 7.75 (1H, m), 7.55 (1H, t, J=8 Hz), 7.5–7.2 (7H, m), 4.4 (1H, d, J=10 Hz), 4.45 (2H, t, J=6 Hz), 3.15 (2H, t, J=6 Hz), 3.05 (1H, m), 2.5 (3H, s), and 1.2 (3H, t, J=4 Hz) ppm; HRMS (M+H)$^+$: 548.2280 m/z.

Example 18

3-[4,5,6,7-Tetrahydro-6-[2'-[[N,N-diethylamino] methyl][1,1'-biphenyl]-4-yl]-3-trifluoromethyl-7-oxo-1H-pyrazolo[3,4-c]pyridin-1-yl]benzamide•TFA This compound was prepared as described for Example 15 with N,N-diethylamine substituted for N,N-dimethylamine in Part C; mp 78.3° C.; $^1$H NMR (CDCl$_3$) δ: 8.1 (1H, m), 7.9–7.7 (3H, m), 7.6–7.4 (5H, m), 7.4–7.3 (3H, m), 4.3 (2H, s), 4.25 (2H, t, J=6 Hz), 3.25 (2H, t, J=6 Hz), 3.1 (2H, m), 2.8 (2H, m) and 1.0 ppm (6H, t, J=8 Hz); HRMS (M+H)$^+$: 562.2431 m/z.

Example 19

3-[4,5,6,7-Tetrahydro-6-[2'-[[pyrrolidin-1-yl]methyl] [1,1'-biphenyl]-4-yl]-3-trifluoromethyl-7-oxo-1H-pyrazolo[3,4-c]pyridin-1-yl]benzamide•TFA This compound was prepared as described for Example 15 with pyrrolidine substituted for N,N-dimethylamine in Part C; mp 174.8° C.; $^1$H NMR (CDCl$_3$) δ: 8.1 (1H, s), 7.9 (1H, d, J=6 Hz), 7.8 (2H, t, J=6 Hz), 7.55 (1H, t, J=6 Hz), 7.45 (5H, m), 7.3 (2H, m), 4.35 (2H, s), 4.25 (2H, t , J=8 Hz), 3.6 (2H, m), 3.2 (2H, t), 2.6 (2H, m), 2.1 (2H, m) and 1.9 ppm (2H, m); HRMS (M+H)$^+$: 560.227 m/z.

Example 20

3-[4,5,6,7-Tetrahydro-6-[2'-[[3(R)-hydroxypyrrolidin-1-yl]methyl][1,1'-biphenyl]-4-yl]-3-trifluoromethyl-7-oxo-1H-pyrazolo[3,4-c]pyridin-1-yl]benzamide•TFA This compound was prepared as described for Example 15 with (R)$_3$-hydroxypyrrolidine substituted for N,N-dimethylamine in Part C; mp 187.6° C.; $^1$H NMR (CDCl$_3$) δ: 8.2–7 (12H, m), 4.5–4.3 (2H, m), 4.2 (2H, t, J=6 Hz) and 3.2 (2H, t, J=6 Hz) ppm; HRMS (M+H)$^+$: 576.2232 m/z.

Example 21

3-[4,5,6,7-Tetrahydro-6-[2'-[[N-propyl-N-methylamino]methyl][1,1'-biphenyl]-4-yl]-3-trifluoromethyl-7-oxo-1H-pyrazolo[3,4-c]pyridin-1-yl]benzamide•TFA This compound was prepared as described for Example 15 with N-methyl-N-propylamine substituted for N,N-dimethylamine in Part C; mp 142.6° C.; $^1$H NMR (CDCl$_3$) δ: 8.0 (1H, s), 7.8 (1H, d, J=7.7 Hz), 7.7 (1H, d, J=7.7 Hz), 7.65 (1H, m), 7.5–7.3 (5H, m), 7.2 (3H, m), 6.7–6.0 (2H, broad), 4.4–4.1 (4H, m), 3.2 (2H, t, J=6 Hz), 2.8 (1H, m), 2.5 (1H, m), 2.15 (3H, s), 1.5 (2H, m), and 0.75 (3H, t, J=8 Hz) ppm; HRMS (M+H)$^+$: 562.2419 m/z.

Example 22

3-[4,5,6,7-Tetrahydro-6-[2'-[[N-t-butylamino] methyl][1,1'-biphenyl]-4-yl]-3-trifluoromethyl-7-oxo-1H-pyrazolo[3,4-c]pyridin-1-yl]benzamide•TFA This compound was prepared as described for Example 15 with t-butylamine substituted for N,N-dimethylamine in Part C; mp 132.7° C.; $^1$H NMR (CDCl$_3$) δ: 8.05 (1H, s), 7.85 (1H, d, J=8 Hz), 7.8 (1H, d, J=8 Hz), 7.7–7.5 (2H, m), 7.45–7.2 (8H, m), 4.2 (2H, t, J=6 Hz), 4.0 (2H, broad), 3.2 (2H, t, J=6 Hz) and 1.2 (9H, s) ppm; HRMS (M+H)$^+$: 562.2436 m/z.

Example 23

3-[4,5,6,7-Tetrahydro-6-[2'-[[2-[[pyridin-3-yl] methyl]pyrrolidin-1-yl]methyl][1,1'-biphenyl]-4-yl]-3-trifluoromethyl-7-oxo-1H-pyrazolo[3,4-c]pyridin-1-yl]benzamide•TFA This compound was prepared as described for Example 15 with 2-[[pyridin-3-yl]methyl]pyrrolidine substituted for N,N-dimethylamine in Part C; mp 124.9° C.; $^1$H NMR (CDCl$_3$) δ: 8.55 (2H, broad s), 8.2 (1H, m), 8.0 (1H, s), 7.8 (1H, d, J=7 Hz), 7.75 (1H, d, J=6 Hz), 7.65 (1H, m), 7.6–7.4 (5H, m), 7.4–7.3 (3H, m), 4.55 (1H, m), 4.3–4.2 (3H, m) and 3.2 (2H, t, J=6 Hz) ppm; HRMS (M+H)$^+$: 651.2690 m/z.

Example 24

3-[4,5,6,7-Tetrahydro-6-[2'-[[N,N-dimethylamino] methyl][1,1'-biphenyl]-4-yl]-3-amido-7-oxo-1H-pyrazolo[3,4-c]pyridin-1-yl]benzamide•TFA Part A:

3-Amidoaniline (5 g, 37 mmol) in HCl (conc., 12 mL) and water (30 mL) was cooled to 0° C. and NaNO$_2$ (2.7 g, 37 mmol) in water (20 mL) was added dropwise. The reaction was stirred for 30 min at 0° C. and a 0° C. solution of NaOAc (9 g, 110.3 mmol) and ethyl 2-chloroacetoacetate (6.2 g, 33 mmol) in EtOH (30 mL) and water (125 mL) was added. The reaction was allowed to warm to ambient temperature over 4 h. The reaction mixture was then filtered and air-dried to give 6.5 g of the desired product (24 mmol, 65%); LRMS (M–H)$^-$: 268 m/z.

Part B:

The 1-chloro-1-carboethoxy hydrazone of 3-amidophenylhydrazine (24.2 mmol, 6.52 g) and N-(4-iodophenyl)-2-morpholino-2-ene-δ-lactam (12.1 mmol, 4.6 g) in toluene (200 mL) and triethylamine (61 mmol, 6.1 g) was heated at reflux for 18 h. The reaction mixture was cooled and evaporated then dissolved in EtOAc, washed with water and brine. This was dried (MgSO$_4$) and evaporated to give an intermediate morpholine adduct (8.62 g). This material was dissolved in CH$_2$Cl$_2$ (100 mL) and TFA (10 mL) then stirred 18 hr at ambient temperature. The reaction was diluted with CH$_2$Cl$_2$ and washed with water. The aqueous layer was back-extracted with additional CH$_2$Cl$_2$ and the combined organic extracts were dried (MgSO$_4$) and evaporated. This material was purified further by flash chromatography eluting with a gradient of hexane:EtOAc ranging from 1:1 to 1:2. There was obtained 3.4 g of product (6.6 mmol, 55%). $^1$H NMR (CDCl$_3$) δ: 8.05 (1H, s), 7.85 (1H, d, J=7.7 Hz), 7.75 (1H, d, J=7.7 Hz), 7.7 (2H, d, J=9 Hz), 7.5 (1H, t, J=7.7 Hz), 7.05 (2H, d, J=9 Hz), 6.3 (1H, broad), 5.8 (1H, broad), 4.45 (2H, q, J=6.9 Hz), 4.05 (2H, t, J=6.9 Hz), 3.35 (2H, t, J=6.9 Hz) and 1.25 (3H, t, J=6.9 Hz) ppm.

Part C:

6-(4-Iodophenyl)-1,4,5,6-tetrahydro-1-(3-amidophenyl)-3-(carboethoxy)-7H-pyrazolo[3,4-c]pyridin-7-one (3.48 g, 6.6 mmol) in 1N NaOH (66 mmol, 66 mL) and THF (200 mL) was heated at reflux for 3 h. The cooled reaction mixture was acidified with conc. HCl to pH 1–2 and partitioned between water and 10% MeOH in EtOAc. The organic layer was dried and evaporated to give 4.1 g of the acid. LRMS (M–H)$^-$: 501 m/z.

The material prepared above (presumed 6.6 mmol) was dissolved in THF (200 mL) and cooled to 0° C. N-methylmorpholine (0.85 g, 8.4 mmol) was added followed by the dropwise addition of isobutyl chloroformate (1.66 g, 12.1 mmol). After 4 hr at 0° C., the reaction mixture was filtered then this solution was placed in a sealed vessel with a 0.5 M solution of $NH_3$ in dioxane (40 mmol, 80 mL). This mixture was stirred at ambient temperature for 18 h. After this time some product had precipitated from the reaction mixture and 1.15 g of material was isolated by filtration (2.3 mmol, 35%). Water was added to the filtrate and the aqueous solution extracted with EtOAc. The EtOAc extracts were washed with brine, dried ($MgSO_4$), and evaporated to give an additional 1.6 g of product (3.2 mmol, 48%, total yield: 5.5 mmol, 83%). $^1H$ NMR (DMSO-$d_6$) δ: 8.1 (1H, s), 8.0 (1H, d, J=7.7 Hz), 7.9–7.75 (3H, m), 7.7–7.5 (2H, m), 7.25 (2H, d, J=9 Hz), 4.1 (2H, t, J=6 Hz) and 3.25 ppm (2H, t, J=6 Hz); LRMS (M+Na)$^+$: 524 m/z.

Part D:

6-(4-Iodophenyl)-1,4,5,6-tetrahydro-1-(3-amidophenyl)-3-(amido)-7H-pyrazolo[3,4-c]pyridin-7-one (1.6 g, 3.1 mmol) and 2-formylphenylboronic acid (1.4 g, 9.4 mmol) in toluene (75 mL), EtOH (75 mL), and 2N $Na_2CO_3$ (15 mL) was purged with $N_2$ for 15 min. Tetrakis (triphenylphosphine) palladium (0.36 g, 0.31 mmol) was added, the inert atmosphere re-established, and the reaction heated at reflux for 18 h. The reaction was evaporated and dissolved in $CHCl_3$ by heating at reflux. The hot solution was filtered to isolate the insoluble crude product. The insoluble product was re-suspended in 10% MeOH in $CHCl_3$ and stirred at ambient temperature for 1 hr, then isolated by filtration. The solid product was purified further by stirring in EtOH (200 mL) for 1 hr followed by filtration and air drying to give 2.73 g of product contaminated with some inorganic salts; $^1H$ NMR (DMSO-$d_6$) δ: 9.9 (1H, s), 8.25 (1H, s), 8.05 (1H, d, J=7.7 Hz), 7.95 (1H, t, J=7.7 Hz), 7.8–7.7 (1H, m), 7.6–7.4 (8H, m), 4.15 (2H, t, J=6 Hz) and 3.2 (2H, t, J=6 Hz) ppm; LRMS (M−H)$^-$: 478 m/z.

Part E:

To 3-[4,5,6,7-tetrahydro-6-[2'-[formyl][1,1'-biphenyl]-4-yl]-3-amido-1H-pyrazolo[3,4-c]pyridin-1-yl]benzamide (0.32 g, 0.67 mmol) in THF (15 mL) and MeOH (15 mL) was added 2.0 M dimethylamine in THF (0.67 mL) with $NaBH_3CN$ (0.042 g, 0.67 mmol) and 0.5 M $ZnCl_2$ in THF (1 mmol, 2 mL). The reaction was stirred at ambient temperature for 18 h. The reaction was evaporated and re-dissolved in 1:1 AcCN:water (4 mL). The product was isolated by preparative HPLC on a C18 column using a gradient of AcCN:water with 0.05% TFA as a gradient. There was obtained 0.104 g of product with a purity of 96% (0.2 mmol, 30%); mp>300° C. $^1H$ NMR (DMSO-$d_6$) δ: 8.1–8.0 (2H, m), 7.95 (1H, d, J=7.7 Hz), 7.8–7.7 (2H, m), 7.6–7.15 (7H, m), 4.1 (2H, t, J=6 Hz), 3.3 (6H, s) and 3.2 (2H, d, J=6 Hz) ppm; HRMS (M+H)$^+$: 509.2308 m/z.

Example 25

3-[4,5,6,7-Tetrahydro-6-[2'-[[N,N-dimethylamino]methyl][1,1'-biphenyl]-4-yl]-3-cyano-7-oxo-1H-pyrazolo[3,4-c]pyridin-1-yl]benzamide•TFA Part A:

The 1-chloro-1-cyano hydrazone of 3-amidophenylhydrazine (6.5 mmol, 1.45 g) and N-(4-iodophenyl)-2-morpholino-2-ene-δ-lactam (5 mmol, 1.92 g) in toluene (20 mL) were heated at reflux and N-methylmorpholine (13.5 mmol, 1.37 g, 1.5 mL) in toluene (50 mL) was added slowly over 1 h. This mixture was heated at reflux for 28 h. The reaction mixture was evaporated, TFA (ca. 10 mL) added, and the solution stirred at ambient temperature for 6 h. The reaction mixture was evaporated, dissolved in EtOAc, filtered, and air-dried. This gave 0.55 g of desired product (1.14 mmol, 23%); $^1H$ NMR (DMSO-$d_6$) δ: 8.1 (1 h, s) 7.95 (1H, d, J=7.7 Hz), 7.8–7.7 (3H, m), 7.55 (2H, t, J=7.7 Hz), 7.15 (2H, d, J=8.4 Hz), 4.1 (2H, t, J=6.2 Hz), 3.15 (2H, t, J=6.2 Hz) and 2.45 ppm (2H, S); LRMS (M+Cl)$^-$: 518.1 m/z.

The EtOAc layer was washed with water, dried ($MgSO_4$) and evaporated to give 0.42 g of impure product.

Part B:

6-(4-Iodophenyl)-1,4,5,6-tetrahydro-1-(3-amidophenyl)-3-(cyano)-7H-pyrazolo[3,4-c]pyridin-7-one (0.55 g, 1.14 mmol), 2-formylphenylboronic acid (0.51 g, 3.42 mmol), and $K_2PO_4$ (solid, 10.2 mmol, 2.2 g) in 1,4-dioxane (50 mL) were purged with $N_2$ for 15 min. Tetrakis (triphenyphosphine) palladium catalyst (240 mg) was added, the inert atmosphere re-established, and the reaction heated at reflux for 18 h. The reaction was cooled to ambient temperature, and the solid removed by filtration. The yellow solution was evaporated and applied to a column of flash silica gel (200 mg) and eluted with 2:1 EtOAc:hexane. There was obtained 0.16 g (0.35 mmol, 31%) of the desired product. $^1H$ NMR (CDCl$_3$) δ: 10.0 (1H, s), 8.1 (1H, s), 8.15 (1H, d, J=7 Hz), 7.9 (1H, d, J=7 Hz), 7.75 (1H, d, J=7 Hz), 7.7–7.6 (3H, m), 7.7–7.6 (5H, m), 4.25 (2H, t, J=6.6 Hz) and 3.15 ppm (2H, t, J=6.6 Hz); LRMS (M+Na)$^+$: 484.2 m/z.

Part C:

3-[4,5,6,7-Tetrahydro-6-[2'-[formyl][1,1'-biphenyl]-4-yl]-3-cyano-7-oxo-1H-pyrazolo[3,4-c]pyridin-1-yl]benzamide (0.16 g, 0.35 mmol) with 2M dimethylamine in THF (2.1 mmol, 1.05 mL), sodium triacetoxyborohydride (0.15 g, 0.7 mmol) and a few drops of acetic acid were stirred in THF (10 mL) for 18 h. This mixture was evaporated, dissolved in EtOAc, washed with water, dried ($MgSO_4$), and evaporated. The final product was purified by preparative HPLC on a C18 column using a gradient of AcCN:water with 0.05% TFA added. There was obtained 123 mg of the desired product as its TFA salt (0.2 mmol, 58%) with a purity of >99% (HPLC); mp 125.5° C.; $^1H$ NMR (CDCl$_3$) δ: 8.1 (1H, s), 7.9 (1H, d, J=7 Hz), 7.8 (1H, d, J=7 Hz), 7.7 (1H, m), 7.6 (1H, t, J=9 Hz), 7.5 (2H, m), 7.4 (2H, d, J=9 Hz), 7.3 (3H, m), 4.3–4.2 (4H, m), 3.2 (2H, t, J=6 Hz) and 2.6 ppm (6H, s); HRMS (M+H)$^+$: 491.2189 m/z.

Example 26

3-[4,5,6,7-Tetrahydro-6-[2'-[[3(R)-hydroxypyrrolidin-1-yl]methyl][1,1'-biphenyl]-4-yl]-3-cyano-7-oxo-1H-pyrazolo[3,4-c]pyridin-1-yl]benzamide•TFA This product was prepared according to Part C of Example 25 with 3(R)-hydroxypyrrolidine substituted for dimethylamine; mp: 161.6° C.; $^1H$ NMR (CD$_3$OD) δ: 8.2 (s, 1H) 8.0 (d, J=8.4 Hz, 1H), 7.8 (d, J=8.0 Hz, 1H) 7.7–7.2 (m, 9H), 5.1 (s, 2H), 4.5 (broad s, 1H), 4.4 (m, 2H), 4.2 (t, J=6.6 Hz, 2H), 4.0–2.8 (m, 2H) and 3.2 ppm (t, J=6.6 Hz); HRMS (M+H)$^+$: 533.2323 m/z.

Example 27

6-(4-{2-[(ethylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt Part A:

Preparation of N-[2-(ethylaminomethyl)]-1H-imidazole. 2-Imidazolecarboxyaldehyde (2.5 g, 26 mmol) was suspended in 100 mL of methanol. Ethylamine (2.0 M in THF) was added. After stirring for 30 minutes at room temperature, NaBH$_4$ (1.98 g, 52 mmol) was added portionwise. The reaction mixture was then heated at 50° C. for 2 h under N$_2$. The solvent was removed. The solid was washed with CH$_2$Cl$_2$ and filtered. The CH$_2$Cl$_2$ solution was dried over MgSO$_4$, concentrated, and dried under vacuum to afford 3.4 g of final product as a yellow oil. $^1$H NMR (CDCl$_3$) δ: 7.04 (s, 2H), 3.91 (s, 2H), 2.69 (q, 2H), 1.12 (t, 3H) ppm.

Part B:

Preparation of ethyl (2Z)-chloro[(4-methoxyphenyl)hydrazono]ethanoate. To p-anisidine (16 g, 0.129 mol) in conc. HCl (40 mL) and 100 mL H$_2$O, cooled to −5° C., was added sodium nitrite (9.4 g, 0.136 mol) in H$_2$O (60 mL). The reaction mixture was stirred at −5° C. for 20 min and a mixture of ethylchloroacetoacetate (22 g, 0.133 mol), ethanol (100 mL), sodiumacetate (32 g, 0.389 mmol), and H$_2$O (400 mL) was added. The reaction was allowed to warm up to room temperature and stirred for 2 h. The product precipitated as a black solid. It was filtered and dried (30 g). $^1$H NMR (CDCl$_3$) δ: 8.28 (s, 1H), 7.18 (d, 2H), 6.90 (d, 2H), 4.41 (q, 2H), 3.80 (s, 3H), 1.42 (t, 3H) ppm.

Part C:

Preparation of ethyl 6-(4-iodophenyl)-1-(4-methoxyphenyl)-7-oxo-4,5,6,7-tetrahydro-1H-pyrazolo[3,4-c]pyridine-3-carboxylate. The product of Part B (30 g, 0.117 mol) was stirred with 1-(4-iodophenyl)-3-(4-morpholinyl)-5,6-dihydro-2 (1H)-pyridinone (29.9 g, 0.078 mol) and triethylamine (74 mL, 0.53 mol) at reflux in toluene (400 mL) for 24 h. The reaction mixture was cooled, washed with water, and dried (Na$_2$SO$_4$). It was concentrated and chromatographed with 1:1 EtOAc/hexane to afford 28.8 g (71%) of the ester-iodo product. MS (M+H)$^+$ 517.9. $^1$H NMR (CDCl$_3$) δ: 7.70 (d, 2H), 7.47 (d, 2H), 7.09 (d, 2H), 6.93 (d, 2H), 4.49 (q, 2H), 4.18 (t, 2H), 3.81 (s, 3H), 3.37 (t, 2H), 1.45 (t, 3H) ppm.

Part D:

Preparation of 6-(4-iodophenyl)-1-(4-methoxyphenyl)-7-oxo-4,5,6,7-tetrahydro-1H-pyrazolo[3,4-c]pyridine-3-carboxamide. Ethyl 6-(4-iodophenyl)-1-(4-methoxyphenyl)-7-oxo-4,5,6,7-tetrahydro-1H-pyrazolo[3,4-c]pyridine-3-carboxylate from Part C (3.0 g, 5.8 mmol) was suspended in 8% NH$_3$ in ethylene glycol (30 mL) in a 100 mL pressure tube. The mixture was heated at 85° C. for 18 hours. Water was added, and the precipitate was filtered and washed with water. The crude product was dried under vacuum to afford 3.2 g of final product. MS (ES$^+$): 489.2 (M+H)$^+$. $^1$H NMR (DMSO-d$_6$) δ: 7.72–7.68 (m, 3H), 7.49–7.41 (m, 3H), 7.15 (d, 2H), 6.97 (d, 2H), 4.00 (t, 2H), 3.77 (s, 3H), 3.16 (t, 2H) ppm.

Part E:

2-(Ethylaminomethyl)imidazole (250 mg, 2 mmol), 6-(4-iodophenyl)-1-(4-methoxyphenyl)-7-oxo-4,5,6,7-tetrahydro-1H-pyrazolo[3,4-c]pyridine-3-carboxamide from Part D (488 mg, 1.02 mmol), CuI (190 mg, 1 mmol), K$_2$CO$_3$ (552 mg, 4 mmol) were added together with 6 mL of DMSO. The mixture was degassed and then heated at 130° C. under N$_2$ for 4 h. The mixture was cooled and aqueous NH$_4$OH (1 mL) was added. The mixture was filtered through Celite® and washed with EtOAc. The two layers were separated and the aqueous layer was extracted with EtOAc. The combined EtOAc mixture was washed with brine, dried over MgSO$_4$, concentrated in vacuo, and chromatographed with MeOH:CHCl$_3$:NH$_4$OH (20:1000:2 to 70:1000:7) to give the desired product. The product was further purified by reverse phase HPLC (C18 reverse phase column, eluted with a H$_2$O/CH$_3$CN gradient with 0.05% TFA) to give 170 mg of the final product as the TFA salt. MS (ES$^+$): 486.5, (M+H)$^+$. $^1$H NMR (CD$_3$OD) δ: 7.56 (d, 2H), 7.49–7.44 (m, 4H), 7.38 (d, 1H), 7.18 (d, 1H), 6.96 (d, 2H), 4.25 (s, 2H), 4.14 (t, 2H), 3.80 (s, 3H), 3.32 (t, 2H), 3.08 (q, 2H), 1.25 (t, 2H) ppm.

Example 28

6-(4-{2-[(Methylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt)

This compound was prepared following the same procedures described in Example 27. MS (ES$^+$): 472.5, (M+H)$^+$. $^1$H NMR (CD$_3$OD) δ: 7.55 (d, 2H), 7.49–7.43 (m, 4H), 7.38 (d, 1H), 7.17 (d, 1H), 6.95 (d, 2H), 4.24 (s, 2H), 4.14 (t, 2H), 3.80 (s, 3H), 3.32 (t, 2H), 2.70 (s, 3H) ppm.

Example 29

6-(4-{2-[(n-propylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt This compound was prepared followed the same procedures described in Part E of Example 27. MS (ES$^+$): 500.5, (M+H)$^+$. $^1$H NMR (CD$_3$OD) δ: 7.56 (d, 2H), 7.49–7.44 (m, 4H), 7.41 (d, 1H), 7.22 (d, 1H), 6.95 (d, 2H), 4.27 (s, 2H), 4.14 (t, 2H), 3.80 (s, 3H), 3.32 (t, 2H), 3.01–2.95 (m, 2H), 1.75–1.60 (m, 2H), 0.95 (t, 3H) ppm.

Example 30

6-(4-{2-[(i-propylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt This compound was prepared followed the same procedures described in Part E of Example 27. MS (ES$^+$): 500.4, (M+H)$^+$. $^1$H NMR (CD$_3$OD) δ: 7.56 (d, 2H), 7.49–7.44 (m, 4H), 7.38 (s, 1H), 7.18 (S, 1H), 6.96 (d, 2H), 4.24 (s, 2H), 4.15 (t, 2H), 3.80 (s, 3H), 3.42–3.38 (m, 1H), 3.32 (t, 2H), 1.26 (d, 6H) ppm.

Example 31

6-(4-{2-[(c-propylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt This compound was prepared followed the same procedures described in Part E of Example 27. MS (ES$^+$): 498.5, (M+H)$^+$. $^1$H NMR (CD$_3$OD) δ: 7.56 (d, 2H), 7.49–7.44 (m, 5H), 7.22 (s, 1H), 6.80 (d, 2H), 4.28 (s, 2H), 4.15 (t, 2H), 3.80 (s, 3H), 3.32 (t, 2H), 2.61 (m, 1H), 0.70 (m, 4H) ppm.

Example 32

6-(4-{2-[(c-propylmethylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt This compound was prepared followed the same procedures described in Part E of Example 27. MS (ES$^+$): 512.6, (M+H)$^+$. $^1$H NMR (CD$_3$OD) δ: 7.56 (d, 2H), 7.49–7.44 (m, 4H), 7.39 (s, 1H), 7.20 (s, 1H), 6.96 (d, 2H), 4.27 (s, 2H), 4.15 (t, 2H), 3.80 (s, 3H), 3.32 (t, 2H), 2.93 (d, 2H), 1.01 (m, 1H), 0.62 (m, 2H), 0.32 (m, 2H) ppm.

Example 33

6-(4-{2-[(c-pentylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid) salt This compound was prepared followed the same procedures described in Part E of Example 27. MS (ES$^+$): 526.6, (M+H)$^+$. $^1$H NMR (CD$_3$OD) δ: 7.56 (d, 2H), 7.49–7.44 (m, 4H), 7.38 (s, 1H), 7.18 (s, 1H), 6.96 (d, 2H), 4.24 (S, 2H), 4.17 (t, 2H), 3.80 (s, 3H), 3.65 (m, 1H), 3.32 (t, 2H), 2.00 (m, 2H), 1.74 (m, 2H), 1.57 (m, 4H) ppm.

Example 34

6-(4-{2-[(n-propylamino)methyl]-1H-imidazol-1-yl}phenyl)-1-(4-methoxyphenyl)-7-oxo-4,5,6,7-tetrahydro-1H-pyrazolo[3,4-c]pyridine-3-carbonitrile, bis(trifluoroacetic acid) salt This compound was prepared followed the same procedures described in Part E of Example 27. MS (ES$^+$): 482.5, (M+H)$^+$. $^1$H NMR (CDCl$_3$) δ: 7.40–7.24 (m, 6H), 7.10 (d, 2H), 6.82 (d, 2H), 4.10 (m, 4H), 3.70 (s, 3H), 3.10 (t, 2H), 2.86 (t, 2H), 1.58 (m, 2H), 0.85 (t, 2H) ppm.

Example 35

6-(4-{2-[(methylamino)methyl]-1H-imidazol-1-yl}phenyl)-1-(4-methoxyphenyl)-7-oxo-4,5,6,7-tetrahydro-1H-pyrazolo[3,4-c]pyridine-3-dimethylcarboxamide, bis(trifluoroacetic acid) salt This compound was prepared followed the same procedures described in Part E of Example 27. MS (ES$^+$): 500.2, (M+H)$^+$ $^1$H NMR (CD$_3$OD) δ: 7.50 (d, 2H), 7.49–7.44 (m, 4H), 7.39 (s, 1H), 7.20 (s, 1H), 6.96 (d, 2H), 4.24 (s, 2H), 4.15 (t, 2H), 3.80 (s, 3H), 3.35 (s, 3H), 3.18 (t, 2H), 3.19 (s, 3H), 2.68 (s, 3H) ppm.

Example 36

1-(4-methoxyphenyl)-6-(4-{2-[(methylamino)methyl]-1H-imidazol-1-yl}phenyl)-3-(methylsulfonyl)-1,4,5,6-tetrahydro-7H-pyrazolo[3,4-c]pyridin-7-one Part A:
Preparation of (1Z)-1-[chloro(methylsulfonyl)methylene]-2-(4-methoxyphenyl)hydrazine. To a solution of p-anisidine (4.39 g, 3.6 mmol) in con. HCl (9.2 mL) and water (20 mL) at 0° C. was slowly added sodium nitrite (2.58 g, 3.7 mmol) in water (20 mL). The reaction mixture was stirred at 0° C. for 0.5 h. The above mixture was poured into a mixture of 3-chloromethanesulphonyl acetone (Grossert, J S, et. al., *Can J. Chem.* 1984, 62, 798)(6.1 g, 3.5 mmol), acetone (50 mL), sodium acetate (6.7 g, 8.2 mmol), and water (100 mL). The resulting mixture was stirred for 4 h at rt. The precipitate was filtered-off and dried to afford the hydrazone as a red solid (5.28 g, 57%); $^1$H NMR (CDCl$_3$) δ: 8.05 (s, 1H), 7.12 (d, 2H), 6.91 (d, 2H), 3.80 (s, 3H), 3.23 (s, 3H) ppm.

Part B:
Preparation of 6-(4-iodophenyl)-1-(4-methoxyphenyl)-3-(methylsulfonyl)-1,4,5,6-tetrahydro-7H-pyrazolo[3,4-c]pyridin-7-one. The product of Part A (2.60 g, 10 mol) was stirred with 1-(4-iodophenyl)-3-(4-morpholinyl)-5,6-dihydro-2(1H)-pyridinone (3.80 g, 10 mol) prepared in Part B of Example 1 and triethylamine (2.76 mL, 20 mol) in EtOAc (30 mL). The mixture was heated at 70° C. under N$_2$ for 12 h. The reaction mixture was cooled to 5° C. and aqueous HCl (12.4 mL of 4N) was added dropwise. The cooling bath was removed and the mixture was stirred at rt for 4 h. A small amount of hexane (5 mL) and water (10 mL) was added. The precipitate formed was filtered, washed with water and hexane, and dried to afford 4.15 g (80%) of the desired product. $^1$H NMR (CDCl$_3$) δ: 7.66 (d, 2H), 7.44 (d, 2H), 7.05 (d, 2H), 6.90 (d, 2H), 4.08 (t, 2H), 3.80 (s, 3H), 3.35 (t, 2H), 3.28 (s, 3H) ppm.

Part C:
Preparation of. 1-(4-methoxyphenyl)-6-(4-{2-[(methylamino)methyl]-1H-imidazol-1-yl}phenyl)-3-(methylsulfonyl)-1,4,5,6-tetrahydro-7H-pyrazolo[3,4-c]pyridin-7-one. The product from Part B (4.15 g, 7.94 mmol), 2-(methylaminmethyl)imidazole (1.93 g, 16.67 mmol), K$_2$CO$_3$ (4.39 g, 31.76 mmol), CuI (1.51 g, 7.94 mmol) were added together with 50 mL of DMSO. The mixture was degassed and then heated at 130° C. under N$_2$ for 4 h. The mixture was cooled and EtOAc and 8% aqueous NH$_4$OH were added. The mixture was filtered through Celite® and washed with EtOAc. The two layers were separated and the aqueous layer was extracted with EtOAc. The aqueous layer was extracted with CHCl$_3$ again. The EtOAc and CHCl$_3$ extracts were washed with water and brine and dried over MgSO$_4$ separately. They were then combined, concentrated, and chromatographed on silica gel with 1:1 EtOAc/hexane and 8:1 CHCl$_3$/MeOH to give 2.79 g of the desired product. This material was further purified by reverse phase HPLC (C18 reverse phase column, eluted with a H$_2$O/CH$_3$CN gradient with 0.05% TFA) to give 2.5 g of the bis-TFA salt. MS (ES$^+$): 507.4, (M+H)$^+$. $^1$H NMR (DMSO-d$_6$) δ: 7.60–7.02 (m, 10H), 4.28 (s, 2H), 4.16 (t, 2H), 3.82 (s, 3H), 3.38 (s, 3H), 3.25 (t, 2H), 2.65 (s, 3H) ppm.

Example 37

6-(4-{2-[(ethylamino)methyl]-1H-imidazol-1-yl}phenyl)-1-(4-methoxyphenyl)-3-(methylsulfonyl)-1,4,5,6-tetrahydro-7H-pyrazolo[3,4-c]pyridin-7-one This compound was prepared followed the same procedures described in Part E of Example 36. MS (ES$^+$): 521.3, (M+H)$^+$. $^1$HNMR (DMSO-d$_6$) δ: 7.60–7.02 (m, 10H), 4.28 (s, 2H), 4.16 (t, 2H), 3.82 (s, 3H), 3.38 (s, 3H), 3.25 (t, 2H), 3.04 (q, 2H), 1.18 (t, 3H) ppm.

Example 38

6-(4-{2-[(i-propylamino)methyl]-1H-imidazol-1-yl}phenyl)-1-(4-methoxyphenyl)-3-(methylsulfonyl)-1,4,5,6-tetrahydro-7H-pyrazolo[3,4-c]pyridin-7-one DPH-215442

This compound was prepared followed the same procedures described in Part E of Example 36. MS (ES$^+$): 535.5, (M+H)$^+$. $^1$H NMR (DMSO-d$_6$) δ: 7.60–7.02 (m, 10H), 4.26 (s, 2H), 4.16 (t, 2H), 3.82 (s, 3H), 3.39 (m, 1H), 3.38 (s, 3H), 3.25 (t, 2H), 1.22 (d, 6H) ppm.

Example 39

6-(4-{2-[(n-propylamino)methyl]-1H-imidazol-1-yl}phenyl)-1-(4-methoxyphenyl)-3-(methylsulfonyl)-1,4,5,6-tetrahydro-7H-pyrazolo[3,4-c]pyridin-7-one This compound was prepared followed the same procedures described in Part E of Example 36. MS (ES$^+$): 535.4, (M+H)+. 1H NMR (DMSO-d6) δ: 7.60–7.02 (m, 10H), 4.28 (s, 2H), 4.16 (t, 2H), 3.82 (s, 3H), 3.38 (s, 3H), 3.25 (t, 2H), 2.95 (t, 2H), 1.60 (m, 2H), 0.87 (t, 3H) ppm.

Numerous modifications and variations of the present invention are possible in light of the above teachings. It is therefore to be understood that within the scope of the appended claims, the invention may be practiced otherwise that as specifically described herein.

What is claimed is:

1. A compound of formula Ia or Ib:

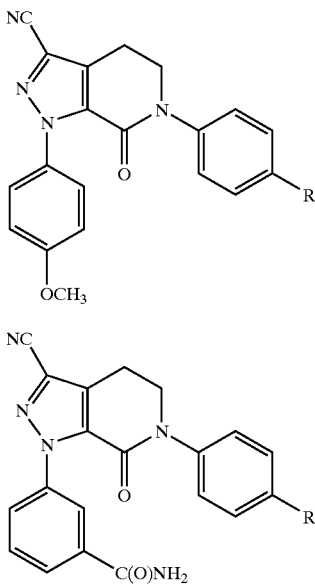

wherein:

R is 2-R$^1$-phenyl or 2-R$^1$-imidazol-1-yl;

R$_1$ is selected from CH$_3$, CH$_2$—NH$_2$, CH$_2$—NHCH$_3$, CH$_2$—NH(CH$_2$CH$_3$), CH$_2$—NH(CH$_2$CH$_2$OH), CH$_2$—NH(CH$_2$CH$_2$CH$_3$), CH$_2$—NH(CH(CH$_3$)$_2$), CH$_2$—NHC(CH$_3$)$_3$, CH$_2$—N(CH$_3$)$_2$, CH$_2$—NCH$_3$(CH$_2$CH$_3$), CH$_2$—NCH$_3$(CH$_2$CH$_2$OH), CH$_2$-NCH$_3$(CH$_2$CH$_2$CH$_3$), CH$_2$—N(CH$_2$CH$_3$)$_2$, CH$_2$—NH-pyrrolidinyl, CH$_2$—NH-(3-hydroxy-pyrroidinyl), CH$_2$—NH-(3-R-hydroxy-pyrrolidinyl), CH$_2$—NH-(3-S-hydroxy-pyrrolidinyl), and CH$_2$—NH-(4-hydroxy-pipericlinyl);

alternatively, R is 3-R$^1$-pyridin-4-yl and R$^1$ is SO$_2$NH$_2$; or a pharmaceutically acceptable salt form tereof.

2. A compound according to claim 1, wherein the compound is of formula Ia or Ib, R is 2-R$^1$-phenyl, and R$^1$ is CH$_2$—N(CH$_3$)$_2$.

3. A compound according to claim 1, wherein the compound is of formula Ia or Ib, R is 2-R$^1$-phenyl, and R$^1$ is CH$_2$—NH-(4-hydroxy-piperidinyl).

4. A compound according to claim 1, wherein the compound is of formula Ia or Ib, R is 2-R$^1$-phenyl, and R$^1$ is CH$_2$—NH-(3-hydroxy-pyrrolidinyl).

5. A compound according to claim 1, wherein the compound is of formula Ia or Ib, R is 2-R$^1$-phenyl, and R$^1$ is CH$_2$—NCH$_3$(CH$_2$CH$_2$OH).

6. A compound according to claim 1, wherein the compound is of formula Ia or Ib, R is 2-R$^1$-phenyl, and R$^1$ is CH$_2$—NH(CH$_2$CH$_2$OH).

7. A compound of formula IIa or IIb:

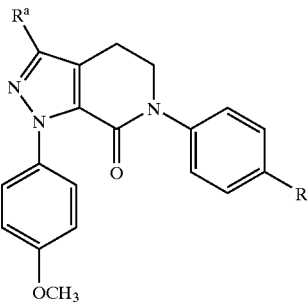

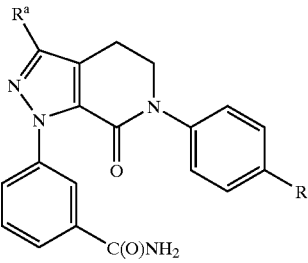

wherein:

R$^a$ is selected from CF$^3$, C(O)NH$_2$, C(O)N(CH$_3$)$_2$, and S(O)$_2$CH$_3$;

R is 2-R$^1$-imidazol-1-yl;

R$^1$ is selected from CH$_3$, CH$_2$—NH$_2$, CH$_2$—NHCH$_3$, CH$_2$—NH(CH$_2$CH$_3$), CH$_2$—NH(CH$_2$CH$_2$CH$_2$OH), CH$_2$—NH(CH$_2$CH$_2$CH$_3$), CH$_2$—NH(CH(CH$_3$)$_2$), CH$_2$—NHC(CH$_3$)$_3$, CH$_2$—N(CH$_3$)$_2$, CH$_2$—NCH$_3$ (CH$_2$CH$_3$), CH$_2$—NCH$_3$(CH$_2$CH$_2$OH), CH$_2$—NCH$_3$ (CH$_2$CH$_2$CH$_3$), CH$_2$—N(CH$_2$CH$_3$)$_2$, CH$_2$—NH-cyclopropyl, CH$_2$—N(CH$_3$)-cyclopropyl, CH$_2$—NH-cyclopentyl, CH$_2$—NH-pyrrolidinyl, CH$_2$—NH-(3-hydroxy-pyrrolidiny), CH$_2$—NH-(3-R-hydroxy-pyrrolidinyl), CH$_2$—NH-(3-S-hydroxy-pyrrolidinyl), CH$_2$—NH-(2-(pyridin-3-yhnethyl)-pyrrolidinyl), and CH$_2$—NH-(4-hydroxy-piperidinyl);

alternatively, R is 3-R$^1$-pyridin-4-yl and R$^1$ is SO$_2$NH$_2$; or a phannaceutically acceptable salt form thereof.

8. A compound according to claim 7, wherein the compound is of fonnula IIb, R$^a$ is CF$_3$, R is 2-R$^1$-imidazol-1-yl, and R$^1$ is CH$_2$—N(CH$_3$)$_2$.

9. A compound according to claim 7, wherein the compound is of formula IIb, R$^a$ is CF$_3$, R is 2-R$^1$-imidazol-1-yl, and R$^1$ is CH$_2$—NH-pyrrolidinyl.

10. A compound according to claim 7, wherein the compound is of formula IIb, R$^a$ is CF$_3$, R is 2-R$^1$-imidazol-1-yl, and R$^1$ is CH$_2$—NH-(3-R-hyroxy-pyrrolidinyl).

11. A compound according to claim 7, wherein the compound is of formula IIb, R$^a$ is CF$_3$, R is 2-R$^1$-imidazol-1-yl, and R$^1$ is CH$_3$.

12. A compound according to claim 7, wherein the compound is of formula IIb, R$^a$ is CF$_3$, R$^a$ is 2-R$^1$-imidazol-1-yl, and R$^1$ is CH$_2$—NHCH$_3$.

13. A compound according to claim 7, wherein the compound is of formula IIb, R$^a$ is CF$_3$, R is 2-R$^1$-imidazol-1-yl, and R$^1$ is CH$_2$—NH-(4-hyclroxy-piperidinyl).

14. A compound according to claim 7, wherein the compound is of formula IIb, R$^a$ is CF$_3$, R is 2-R$^1$-imidazol-1-yl, and R$^1$ is CH$_2$—NH-(3-S-hydroxy-pyrrolidinyl).

15. A compound according to claim 7, wherein the compound is of formula IIb, R$^a$ is C(O)NH$_2$, R is 3-R$^1$-pyridin-4-yl, and R$^1$ is SO$_2$NH$_2$.

16. A compound according to claim 7, wherein the compound is of formula IIa, $R^a$ is $CF_3$, R is 2-$R^1$-iniidazol-1-yl, and $R^1$ is $CH_2$—NH-(3-hydroxy-pyrrolidinyl).

17. A compound according to claim 7, wherein the compound is of formula IIa, $R^a$ is $CF_3$, R is 2-$R^1$-imidazol-1-yl, and $R^1$ is $CH_2$—N(CH_3)_2.

18. A compound according to claim 7, wherein the compound is of formula IIa, $R^a$ is $C(O)NR^2$, R is 2-$R^1$-iniidazol-1-yl, and $R^1$ is $CH_2$—N(CH_3)_2.

19. A compound according to claim 7, wherein the compound is of formula IIa, $R^a$ is $CF_3$, R is 2-$R^1$-imidazol-1-yl, and $R^1$ is $CH_2$—NH-pyrrolidinyl.

20. A compound according to claim 7, wherein the compound is of fonnula IIa, $R^a$ is $C(O)NH_2$, R is 2-$R^1$-imidazol-1-yl, and $R^1$ is $CH_2$—NH-pyrrolidinyl.

21. A compound according to claim 7, wherein the compound is of formula IIa, $R^1$ is $CF_3$, R is 2-$R^1$-imidazol-1-yl, and $R^1$ is $CH_2$—NH-(3-R-hydroxy-pyrrolidinyl).

22. A compound according to claim 7, wherein the compound is of formula IIa, $R^a$ is $C(O)NH_2$, R is 2-$R^1$-imidazol-1-yl, and $R^1$ is $CH_2$—NH-(3-R-hydroxy-pyrrolidinyl).

23. A compound according to claim 7, wherein the compound is of formula IIa, $R^a$ is $CF_3$, R is 2-$R^1$-imidazol-1-yl, and $R^1$ is $CH_2$—NH-(3-S-hydroxy-pyrrolidinyl).

24. A compound according to claim 7, wherein the compound is of formula IIa, $R^a$ is $C(O)NR_2$, R is 2-$R^1$-imidazol-1-yl, and $R^1$ is $CH_2$—NH-(3-S-hyciroxy-pyrrolidinyl).

25. A compound according to claim 7, wherein the compound is of formula IIa, $R^a$ is $CF_3$, R is 2-$R^1$-imidazol-1-yl, and $R^1$ is $CH_3$.

26. A compound according to claim 7, wherein the compound is of formula IIa, $R^a$ is $C(O)NH_2$, R is 2-$R^1$-imidazol-1-yl, and $R^1$ is $CH_3$.

27. A compound according to claim 7, wherein the compound is of formula IIa, $R^a$ is $CF_3$, R is 2-$R^1$-imidazol-1-yl, and $R^1$ is $CH_2$—NHCH_3.

28. A compound according to claim 7, wherein the compound is of formula IIa, $R^a$ is $C(O)NH_2$, R is 2-$R^1$-iniidazol-1-yl, and $R^1$ is $CH_2$—NH(CH_3).

29. A compound according to claim 7, wherein the compound is of formula IIa, $R^a$ is $CF_3$, R is 2-$R^1$-imidazol-1-yl, and $R^1$ is $CH_2$—NH-(4-hydroxy-piperidinyl).

30. A compound according to claim 7, wherein the compound is of formula IIa, $R^a$ is $C(O)NH_2$, R is 2-$R^1$-imidazol-1-yl, and $R^1$ is $CH_2$—NH-(4-hydroxy-piperidinyl).

31. A compound of formula IIIa or IIIb:

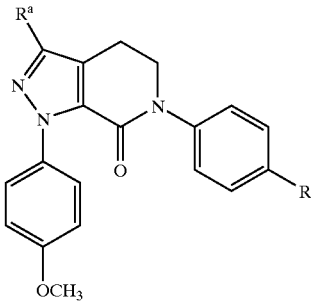

IIIa

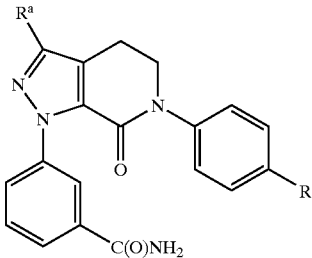

IIIb wherein:
$R^a$ is $CF_3$ or $C(O)NH_2$;
R is 2-$R^1$-phenyl;
$R^1$ is selected from $CH_3$, $CH_2$—NH(CH_2CH_3), $CH_2$—NH(CH_2CH_2OH), $CH_2$—NH(CH_2CH_2CH_3), $CH_2$—NH(CH(CH_3)_2), $CH_2$—NHC(CH_3)_3, $CH_2$—NCH_3(CH_3), $CH_2$—NCH_3(CH_2CH_2OH), $CH_2$—NCH_3(CH_2CH_3), $CH_2$—N(CH_2CH_3)_2, $CH_2$—NH-pyrrolidinyl, $CH_2$—NH-(3-hydroxy-pyrrolidinyl), $CH_2$—NH-(3-R-hydroxy-pyrrolidinyl), $CH_2$—NH-(3-S-hydroxy-pyrrolidinyl), $CH_2$—NH-(2-pyridin-3-ylmethyl)-pyrrolidinyl), and $CH_2$—NH-(4-hydroxy-pipcridinyl);
alternatively, R is 3-$R^1$-pyridin-4-yl and $R^1$ is $SO_2NH_2$;
or a pharmaceutically acceptable salt form thereof.

32. A compound according to claim 31, wherein the compound is of formula IIIb, $R^a$ is $CF_3$, R is 2-$R^1$-phenyl, and $R^1$ is CH2—NH-(4-hydroxy-piperidinyl).

33. A compound according to claim 31, wherein the compound is of formula IIIb, $R^a$ is $CF_3$, R is 2-$R^1$-phenyl, and $R^1$ is $CH_2$—NCH_3(CH_2CH_3).

34. A compound according to claim 31, wherein the compound is of formula IIIb, $R^a$ is $CF_3$, R is 2-$R^1$-phenyl, and $R^1$ is $CH_2$—N(CH_2CH_3)_2.

35. A compound according to claim 31, wherein the compound is of formula IIIb, $R^a$ is $CF_3$, R is 2-$R^1$-phenyl, and $R^1$ is $CH_2$—NH-pyrrolidinyl.

36. A compound according to claim 31, wherein the compound is of formula IIIb, $R^a$ is $CF_3$, R is 2-$R^1$-phenyl and $R^1$ is $CH_2$—NH-(3-R-hydroxy-pyrrolidinyl).

37. A compound according to claim 31, wherein the compound is of formula IIIb, $R^a$ is $CF_3$, R is 2-$R^1$-phenyl and $R^1$ is $CH_2$—NH-(3-S-hydroxy-pyrrolidinyl).

38. A compousd according to claim 31, wherein the compound is of formula IIIb, $R^a$ is $CF_3$, R is 2-$R^1$-phenyl, and $R^1$ is $CH_2$—NCH_3(CH_2CH_2CH_3).

39. A compound according to claim 31, wherein the compound is of formula IIIb, $R^a$ is $CF_3$, R is 2-$R^1$-phenyl, and $R^1$ is $CH_2$—NRC(CF_3)_3.

40. A compound according to claim 31, wherein the compound is of formula IIIb, $R^a$ is $CF_3$, R is 2-$R^1$-phenyl, and $R^1$ is $CH_2$—NH-(2-(pyridin-3-ylmettyl)-pyrrolidinyl).

41. A compound according to claim 31, wherein the compound is of formula IIIa, $R^a$ is $CF_3$, R is 2-$R^1$-phenyl, and $R^1$ is $CH_2$—NH-(3-R-hydroxy-pyrrolidinyl).

42. A compound according to claim 31, wherein the compound is of formula IIIa, $R^a$ is $CF_3$, R is 2-$R^1$-phenyl, and $R^1$ is $CH_2$—NH-(3-hydroxy-pyrrolidinyl).

43. A compound according to claim 31, wherein the compound is of formula IIIa, $R^a$ is $CF_3$, R is 2-$R^1$-phenyl and $R^1$ is $CH_2$—NH-(3-S-hydroxy-pyrrolidinyl).

44. A compound according to claim 31, wherein the compound is of formula IIIa, $R^a$ is $CF_3$, R is 2-$R^1$-phenyl, and $R^1$ is $CH_2$—NH-(4-hydroxy-piperidhlyl).

45. A compound according to claim 31, wherein the compound is of formula IIIa, $R^a$ is C(O)NH$_2$, R is 2-R$^1$-phenyl, and R$^1$ is CH$_2$—NH-(3-R-hydroxy-pyrrolidinyl).

46. A compound according to claim 31, wherein the compound is of formula IIIa, $R^a$ is CF$_3$, R is 2-R$^1$-phenyl and R$^1$ is CH$_2$—NH-(3-S-hydroxy-pyrrolidinyl).

47. A compound according to claim 31, wherein the compound is of fonnula IIIa, $R^a$ is C(O)NH$_2$, R is 2-R$^1$-phenyl, and R$^1$ is CH$_2$—NH-(4-hydroxy-piperidinyl).

48. A compound according to claim 1, wherein the compound is of formula Ia, R is 2-R$^1$-imidazol-1-yl, and R$^1$ is CH$_2$—NH(CH$_2$CH$_2$CH$_3$).

49. A compound according to claim 7, wherein the compound is of formula IIa, $R^a$ is C(O)N(CH$_3$)$_2$, R is 2-R$^1$-imidazol-1-yl, and R$^1$ is CH$_2$—NHCH$_3$.

50. A compound according to claim 7, wherein the compound is of formula IIa, $R^a$ is C(O)NH$_2$, R is 2-R$^1$-imidazol-1-yl, and R$^1$ is CH$_2$—NHCH$_3$.

51. A compound according to claim 7, wherein the compound is of formula IIa, $R^a$ is S(O)$_2$CF$_3$, R is 2-R$^1$-imidazol-1-yl, and R$^1$ is CH$_2$—NHCH$_3$.

52. A compound according to claim 7, wherein the compound is of formula IIa, $R^a$ is C(O)NH$_2$, R is 2-R$^1$-imidazol-1-yl, and R$^1$ is CH$_2$—NHCH$_2$CH$_3$.

53. A compound according to claim 7, wherein the compound is of formula IIa, $R^a$ is C(O)NH$_2$, R is 2-R$^1$-imidazol-1-yl, and R$^1$ is CH$_2$—NHCH(CH$_3$)$_2$.

54. A compound according to claim 7, wherein the compound is of formula IIa, $R^a$ is C(O)NH$_2$, R is 2-R$^1$-imidazol-1-yl, and R$^1$ is CH$_2$—NHCH$_2$CH$_2$CH$_3$.

55. A compound according to claim 7, wherein the compound is of formula IIa, $R^a$ is S(O)$_2$CH$_3$, R is 2-R$^1$-imidazol-1-yl, and R$^1$ is CH$_2$—NHCH$_2$CH$_3$.

56. A compound according to claim 7, wherein the compound is of formula IIa, $R^a$ is S(O)$_2$CH$_3$, R is 2-R$^1$-imidazol-1-yl, and R$^1$ is CH$_2$—NHCH$_2$CH$_2$CH$_3$.

57. A compound according to claim 7, wherein the compound is of formula IIa, $R^a$ is S(O)$_2$CH$_3$, R is 2-R$^1$-imidazol-1-yl, and R$^1$ is CH$_2$—NHCH(CH$_3$)$_2$.

58. A compound according to claim 7, wherein the compound is of formula IIa, $R^a$ is S(O)$_2$CH$_3$, R is 2-R$^1$-imidazol-1-yl, and R$^1$ is CH$_2$—NH-cyclopropyl.

59. A compound according to claim 7, wherein the compound is of formula IIa, $R^a$ is C(O)NH$_2$, R is 2-R$^1$-imidazol-1-yl, and R$^1$ is CH$_2$—NH-cyclopropyl.

60. A compound according to claim 7, wherein the compound is of formula IIa, $R^a$ is C(O)NH$_2$, R is 2-R$^1$-imidazol-1-yl, and R$^1$ is CH$_2$—N(CH$_3$)-cyclopropyl.

61. A compound according to claim 7, wherein the compound is of formula IIa, $R^a$ is C(O)NH$_2$, R is 2-R$^1$-imidazol-1-yl, and R$^1$ is CH$_2$—NH-cyclopentyl.

62. A pharmaceutical composition, comprising: a pharmaceutically acceptable carrier and a therapeutically effective amount of a compound according to claim 1 or a pharmaceutically acceptable salt form thereof.

63. A method for treating a thrombocinbolic disorder, comprising: administering to a patient in need thereof a therapeutically effective amount of a compound according to claim 1 or a pharmaceutically acceptable salt form thereof.

64. A method according to claim 63, wherein the thromboembolic disorder is selected from the group consisting of arterial cardiovascular thromboembolic disorders, venous cardiovasculax thromboembolic disorders, arterial cerebrovasculnr thromboembolie disorders, and venous cerebrovascular thromboembolic disorders.

65. A method according to claim 64, wherein the throinboembolic disorder is selected unstable angina, first myocardial infarction, recurrent myocardial infarction, lachemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, and (e) hemodialysis.

* * * * *